(12) United States Patent
Kim

(10) Patent No.: US 7,829,667 B2
(45) Date of Patent: *Nov. 9, 2010

(54) ANTI-OBESE IMMUNOGENIC HYBRID POLYPEPTIDES AND ANTI-OBESE VACCINE COMPOSITION COMPRISING THE SAME

(75) Inventor: Hyo-Joon Kim, Ansan-si (KR)

(73) Assignee: SJ Biomed, Inc., Ansan-si, Gyeonggi-do (KR)

( * ) Notice: Subject to any disclaimer, the term of this patent is extended or adjusted under 35 U.S.C. 154(b) by 681 days.

This patent is subject to a terminal disclaimer.

(21) Appl. No.: 10/593,413

(22) PCT Filed: Mar. 18, 2005

(86) PCT No.: PCT/KR2005/000784

§ 371 (c)(1),
(2), (4) Date: Sep. 18, 2006

(87) PCT Pub. No.: WO2005/087800

PCT Pub. Date: Sep. 22, 2005

(65) Prior Publication Data

US 2010/0240575 A1      Sep. 23, 2010

(30) Foreign Application Priority Data

Mar. 18, 2004   (KR) .................. 10-2004-0018551

(51) Int. Cl.
C07K 14/435   (2006.01)
C07K 14/775   (2006.01)
A61K 39/00    (2006.01)

(52) U.S. Cl. ................ 530/326; 530/300; 530/350; 435/69.1

(58) Field of Classification Search .......... None
See application file for complete search history.

(56) References Cited

U.S. PATENT DOCUMENTS 5,843,446 A   12/1998 Ladd 6,284,533 B1   9/2001 Thomas
6,541,011 B2 *  4/2003 Punnonen et al. ......... 424/204.1

FOREIGN PATENT DOCUMENTS

| CN | 1392798 A | 1/2003 |
| EP | 0406316 B1 | 1/1995 |
| KR | 1020020018971 A | 3/2002 |
| WO | WO/02/20040 * | 3/2002 |
| WO | WO03015812 | 2/2003 |
| WO | WO2004001997 | 3/2004 |

OTHER PUBLICATIONS

Walley AJ, et al. "The genetic contribution to non-syndromic human obesity." Nat Rev Genet. Jul. 2009;10(7):431-42.*

Leclerc, C., et al; Immunodominance of a Recombinant T-Cell Epitope Depends on its Molecular Environment; Molecular Immunology, vol. 30, No. 17, pp. 1561-1572; 1993.

Pfitzner, R., et al; Isolation, Expression and Characterization of a Human Apoliporotein B 100-Specific cDNA Clone; Biol. Chem.; vol. 367, pp. 1077-1083; Oct. 1986.

Wu, R., et al; Autoantibodies to OxLDL are decreased in individuals with borderline hypertension; Hypertension Journal of the American Heart Association; Online ISSN: 1524-4563.

Partidos, C., et al. The effect of orientation of epitopes on the immunogenicity of chimeric synthetic peptides representing measles virus protein sequences; Molecular Immunology; vol. 29, No. 5, pp. 651-658; 1992.

Francis, M., et al; Non-responsiveness to a foot-and-mouth disease virus peptide overcome by addition of foreign helper T-cell determinants. Nature, vol. 300; November.

Palinski, W., et al; Immunization of low density lipoprotein (LDL) receptor-deficient rabbits with homologous malondialdhyde-modified LDL reduces atherogenesis. Proc. Natl. Acad. Sci. USA, vol. 92, pp. 821-825; Jan. 1995.

Bailey, J.M.; Cholesterol Vaccines; Science, vol. 264; May 1994.

* cited by examiner

*Primary Examiner*—Bo Peng
(74) *Attorney, Agent, or Firm*—Kohn & Associates, PLLC

(57) ABSTRACT

Disclosed is an immunogenic hybrid polypeptide comprising a mimetic peptide of a B cell epitope of apolipoprotein B-100 and a helper T cell epitope, the mimetic peptide being fused at its C-terminus to an N-terminus of the helper T cell epitope. Also disclosed is a vaccine composition for preventing or treating obesity comprising the polypeptide.

11 Claims, 11 Drawing Sheets

FIGURE 2

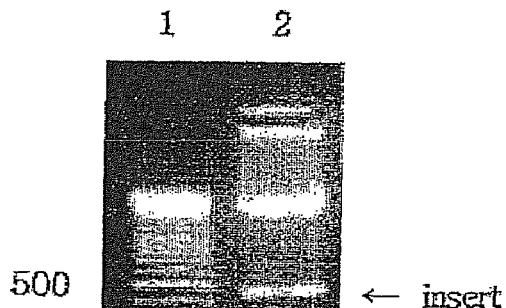

FIGURE 3

```
Start                           6X His                                                      pBL
Met  Arg  Gly  Ser  His  His  His  His  His  His  Gly  Ser  Asp  Asp  Asp  Asp  Lys  Ile  Val  Asp
ATG  AGA  GGA  TCG  CAT  CAC  CAT  CAC  CAT  CAC  GGA  TCC  GAT  GAT  GAT  GAC  AAG  ATC  GTC  GAC Arg  Asn  Val  Pro  Pro  Ile  Phe  Asn  Asp  Val  Tyr  Trp  Ile  Ala  Phe  Leu  Asp  Arg  Asn  Val
CGT  AAT  GTT  CCT  CCT  ATC  TTC  AAT  GAT  GTT  TAT  TGG  ATT  GCA  TTC  CTC  GAC  CGT  AAT  GTT Pro  Pro  Ile  Phe  Asn  Asp  Val  Tyr  Trp  Ile  Ala  Phe  Leu  Asp  Arg  Asn  Val  Pro  Pro  Ile
CCT  CCT  ATC  TTC  AAT  GAT  GTT  TAT  TGG  ATT  GCA  TTC  CTC  GAC  CGT  AAT  GTT  CCT  CCT  ATC Phe  Asn  Asp  Val  Tyr  Trp  Ile  Ala  Phe  Leu  Asp  Arg  Asn  Val  Pro  Pro  Ile  Phe  Asn  Asp
TTC  AAT  GAT  GTT  TAT  TGG  ATT  GCA  TTC  CTC  GAC  CGT  AAT  GTT  CCT  CCT  ATC  TTC  AAT  GAT Val  Tyr  Trp  Ile  Ala  Phe  Leu  Asp  Met  Gln  Trp  Asn  Ser  Thr  Thr  Phe  His  Gln  Ala  Leu
GTT  TAT  TGG  ATT  GCA  TTC  CTC  GAC  ATG  CAG  TGG  AAC  TCC  ACC  ACA  TTC  CAC  CAA  GCT  CTG Leu  Asp  Pro  Arg  Val  Arg  Gly  Leu  Tyr  Phe  Pro  Ala  Gly  Gly  Ser  Ser  Ser  Gly  Thr  Val
CTA  GAT  CCC  AGA  GTG  AGG  GGC  CTA  TAT  TTT  CCT  GCT  GGT  GGC  TCC  AGT  TCC  GGA  ACA  GTA Asn  Pro  Val  Pro  Thr  Thr  Ala  Ser  Pro  Ile  Ser  Ser  Ile  Phe  Ser  Arg  Thr  Gly  Asp  Pro
AAC  CCT  GTT  CCG  ACT  ACT  GCC  TCA  CCC  ATA  TCG  TCA  ATC  TTC  TCG  AGG  ACT  GGG  GAC  CCT Ala  Pro  Asn  Leu  Glu  Arg  Ser  Stop
GCA  CCG  AAC  CTC  GAG  CGG  TCA  TAA  GCC  GAA  TTC  CAG  CAC  ACT  GGC  GGC  CGT  TAC  TAG  TGG

ATC  CGA  GCT  CGG  TAC  CAA  GCT
```

FIGURE 8
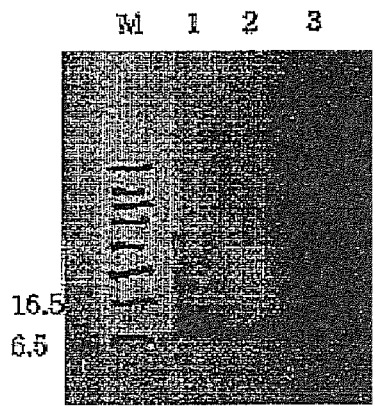
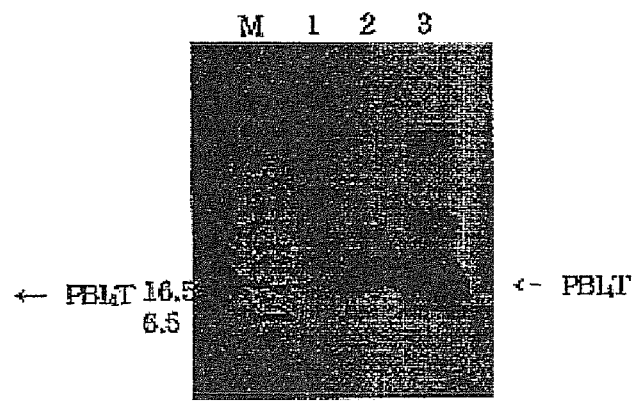
FIGURE 9
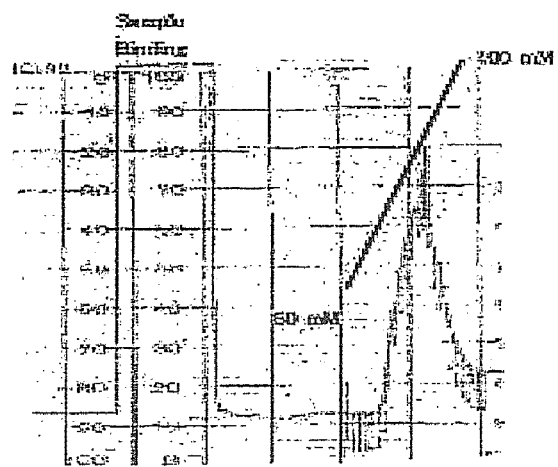
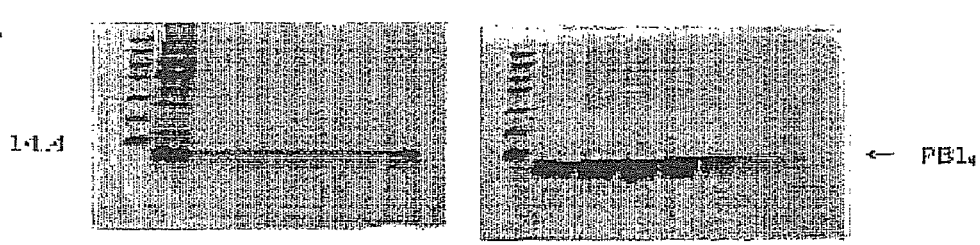

FIGURE 13
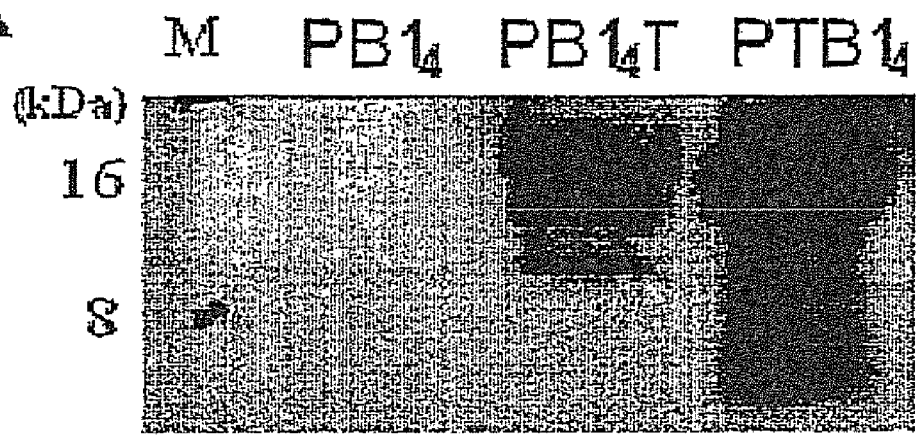
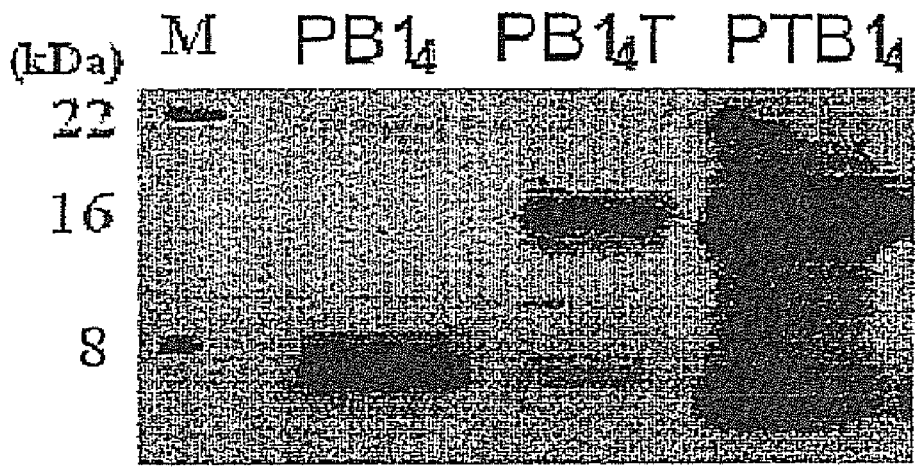

FIGURE 14

Met Arg Gly Ser His His His His His His Gly Ser Asp Asp Asp Asp
ATG AGA GGA TCG CAT CAC CAT CAC CAT CAC GGA TCC GAT GAT GAT GAC
                        His tag Lys Ile Val Asp Met Gln Trp Asn Ser Thr Thr Phe His Gln Ala Leu
AAG ATC GTC GAC ATG CAG TGG AAC TCC ACC ACA TTC CAC CAA GCT CTG
                  ↳       preS2

Leu Asp Pro Arg Val Arg Gly Leu Tyr Phe Pro Ala Gly Gly Ser Ser
CTA GAT CCC AGA GTG AGG GGC CTA TAT TTT CCT GCT GGT GGC TCC AGT

Ser Gly Thr Val Asn Pro Val Pro Thr Thr Ala Ser Pro Ile Ser
TCC GGA ACA GTA AAC CCT GTT CCG ACT ACT GCC TCA CCC ATA TCG

Ser Ile Phe Ser Lys Thy Gly Asp Pro Ala Pro Asn Leu Asp Arg
TCA ATC TTC TCG AAG ACT GGG GAC CCT GCA CCG AAC CTC GAC CGT
                              preS2            ↲ linker ↳

Asn Val Pro Pro Ile Phe Asn Asp Val Tyr Trp Ile Ala Phe Leu
AAT GTT CCT CCT ATC TTC AAT GAT GTT TAT TGG ATT GCA TTC CTC
         PB1                                              ↲ linker Asp Arg Asn Val Pro Pro Ile Phe Asn Asp Val Tyr Trp Ile Ala
GAC CGT AAT GTT CCT CCT ATC TTC AAT GAT GTT TAT TGG ATT GCA
    ↳       PB1

Phe Leu Asp Arg Asn Val Pro Pro Ile Phe Asn Asp Val Tyr Trp
TTC CTC GAC CGT AAT GTT CCT CCT ATC TTC AAT GAT GTT TAT TGG
    ↲ linker ↳       PB1

Ile Ala Phe Leu Asp Arg Asn Val Pro Pro Ile Phe Asn Asp Val
ATT GCA TTC CTC GAC CGT AAT GTT CCT CCT ATC TTC AAT GAT GTT
            ↲ linker ↳       PB1

Tyr Trp Ile Ala Phe Stop
TAT TGG ATT GCA TTC TAA

US 7,829,667 B2

ANTI-OBESE IMMUNOGENIC HYBRID POLYPEPTIDES AND ANTI-OBESE VACCINE COMPOSITION COMPRISING THE SAME

CROSS-REFERENCE TO RELATED APPLICATIONS

This is a National Phase Filing Under 35 U.S.C. 371, of International Application No. PCT/KR05/000784, filed Mar. 18, 2005, which claims the benefit of priority of Korean Patent Application No. 10-2004-0018551, filed Mar. 18, 2004, both of which are incorporated herein by reference.

TECHNICAL FIELD

The present invention relates to an immunogenic hybrid polypeptide, which comprises an amino acid sequence of a mimetic peptide of a B cell epitope of apolipoprotein B-100 and in which a C-terminus of the mimetic peptide is fused to an N-terminus of a helper T cell epitope, and a vaccine composition for preventing or treating obesity comprising the same.

BACKGROUND ART

Recently, arteriosclerosis and coronary atherosclerotic disease (CAD) have been gradually increasing in Korea due to a shift to Western dietary habits, and are the leading cause of increased mortality. Serum lipids causing these diseases include cholesterol, triglycerides (TG), free fatty acids and phospholipids. They form lipoproteins with apolipoproteins and Ere transported through the bloodstream. Among them, low density lipoproteins (LDL) function to transport mainly TG and cholesterol, and changes in LDL-cholesterol levels are indications of the prognosis of the diseases.

LDL-cholesterol, which is a major factor of lipid metabolism-associated diseases of adult people, binds to LDL receptors on the plasma membrane of cells in each tissue and is stored and used in the tissue. Alternatively, LDL-cholesterol is taken up by scavenger cells and hydrolyzed, and free cholesterol is transferred to HDL along with apo E lipoprotein to be recycled in the liver, or is converted to bile salt to be discharged. During this process, the apolipoprotein performs very important functions to maintain structural homeostasis of lipoproteins, serves as a cofactor of the enzyme lipoprotein lipase, and plays a critical role in binding to a specific receptor on the plasma membrane.

Apolipoprotein B-100 (Apo B-100) is a major protein component of LDL, and is also present in IDL and VLDL. Thus, when antibodies in the blood are induced to recognize apo B-100, LDL clearance by phagocytes will easily occur. In this regard, some recent studies have been focused on the employment of vaccines to decrease plasma LDL-cholesterol levels and reduce the incidence of arteriosclerosis. Antibodies induced by such anti-cholesterol vaccine therapy are IgM types which are considered to bind to VLDL, IDL and LDL, and such a strategy suggests the possibility of developing vaccines for preventing and treating hypercholesterolemia and atherosclerosis (Bailey, et al., Cholesterol vaccines. *Science* 264, 1067-1068, 1994; Palinski W et al., *Proc Natl Acad Sci U.S.A.* 92, 821-5, 1995; Wu R, de Faire U et al., *Hypertension*. 33, 53-9, 1999). Also, apolipoprotein B-100 is a huge protein molecule, which consists of 4560 amino acid residues, contains signal peptide of 24 amino acid residues and has a molecular weight of more than 500 kDa (Elovson J et al., *Biochemistry*, 24:1569-1578, 1985). Since apolipoprotein B-100 is secreted mainly by the liver and is an amphipathic molecule, it can interact with the lipid components of plasma lipoproteins and an aqueous environment (Segrest J. P et al., *Adv. Protein Chem.*, 45:303-369, 1994). Apolipoprotein B-100 stabilizes the size and structure of LDL particles and plays a critical role in controlling the homeostasis of plasma LDL-cholesterol through binding to its receptor (Brown M S et al., *Science*, 232:34-47, 1986).

Korean Pat. Laid-open Publication No. 2002-0018971, which was filed by the present inventors, describes a mimetic peptide of an epitope of apo B-100 having an anti-obesity effect. However, this publication only discloses that the mimetic peptide of the B cell epitope has an anti-obesity effect.

Prior to the present invention, there is no report of enhancing the immunogenicity of an apolipoprotein by fusing a B cell epitope of the apolipoprotein and a T cell epitope, except for an attempt to enhance immune responses by employing a protein carrier or adjuvant.

As described in U.S. Pat. No. 5,843,446, when luteinizing hormone releasing hormone (LHRH) is conjugated with a different protein to enhance the immunogenicity of LHRH, the majority of immune responses are directed to the carrier protein rather than to LHRH, leading to carrier-induced immune suppression. Thus, persistent effort is required for selecting additional materials and determining linkage patterns and linkage sites capable of enhancing the immunogenicity of B cell epitopes.

Many attempts to fuse a hapten with a carrier protein were made to enhance the immunogenicity of the hapten, but failed to obtain uniform enhancing effects. In particular, the linear linkage of a B cell epitope and a T cell epitope, like the present invention, resulted in loss of immunogenicity according to the orientation of the epitopes, the type of each epitope, and the like (Francis, M. J. et al., *Nature* 330:168-170, 1987), and the presence of a linker brought about reduced antigenicity (Partidos, C. et al., *Mol. Immunol.* 29:651-658, 1992). That is, there is no consistent rule applicable to design peptide vaccines, and the efficacy of designed vaccines is also not predictable. For the same reasons, when a highly hydrophobic $PB1_4$ peptide, which is an apo-B mimetic peptide, is fused with a T cell epitope, an antigenic region can be internalized into the fusion protein, leading to a decrease in its ability to induce antibody responses.

Based on this background, the present inventors made various attempts to enhance the immunogenicity of $PB1_4$, which is a mimetic peptide of a B cell epitope of apolipoprotein B-100 having an anti-obesity effect. As a result, a hybrid polypeptide, in which an N-terminus of a helper T cell epitope is fused to a C-terminus of the mimetic peptide, displayed an excellent immunoenhancing effect, indicating that it is effective for preventing or treating obesity. It was an unexpected result since hybrid polypeptides displays excellent anti-obesity activity without inducing immune responses that neutralize beneficial activities or effects of the B cell epitope of apolipoprotein B-100 or without causing harmful side effects.

SUMMARY OF THE INVENTION

In one aspect, the present invention provides an immunogenic hybrid polypeptide, which comprises an amino acid sequence of a mimetic peptide of a B cell epitope of apolipoprotein B-100 and in which a C-terminus of the mimetic peptide is fused to an N-terminus of a helper T cell epitope.

In another aspect, the present invention provides a vaccine for preventing or treating obesity, comprising an immunogenic hybrid polypeptide, which comprises an amino acid sequence of a mimetic peptide of a B cell epitope of apolipoprotein B-100 and in which a C-terminus of the mimetic peptide is fused to an N-terminus of a helper T cell epitope.

In a further aspect, the present invention provides a recombinant vector comprising a gene encoding the immunogenic hybrid polypeptide, a transformant comprising the recombinant vector, and a method of producing the hybrid polypeptide by culturing a host cell transformed with the recombinant vector.

BRIEF DESCRIPTION OF THE DRAWINGS

The above and other objects, features and other advantages of the present invention will be more clearly understood from the following detailed description taken in conjunction with the accompanying drawings, in which:

FIG. 2 shows the results of digestion of $pB1_4T$ with restriction enzymes;

FIG. 3 shows a DNA sequence of $pB1_4T$ and an amino acid sequence predicted therefrom;

FIG. 8 shows the results of Western blotting for purified $PB1_4T$ with a rabbit anti-$PB1_4$ antibody (A) and an anti-preS2 monoclonal antibody (B) (lane 1: *E. coli* M15; lane 2: *E. coli* $M15/pB1_4T$ not induced with IPTG; lane 3: IPTG-induced *E. coli* $M15/pB1_4T$, collected 3 hrs after IPTG induction);

FIG. 9 shows the $PB1_4$ elution profile resulting from Ni-NTA affinity chromatography according to a linear imidazole gradient;

FIG. 13 shows the results of Western blotting for purified $PB1_4$, $PB1_4T$ and $PTB1_4$ with a mouse anti-preS2 monoclonal antibody and an HRP-conjugated goat anti-mouse IgG antibody (A) and with an anti-$PB1_4$ anti-serum and an HRP-conjugated goat anti-rabbit IgG antibody (B);

FIG. 14 shows a DNA sequence of $TB1_4/pQE30$ and an amino acid sequence predicted therefrom;

BEST MODE FOR CARRYING OUT THE INVENTION

Figure 1:
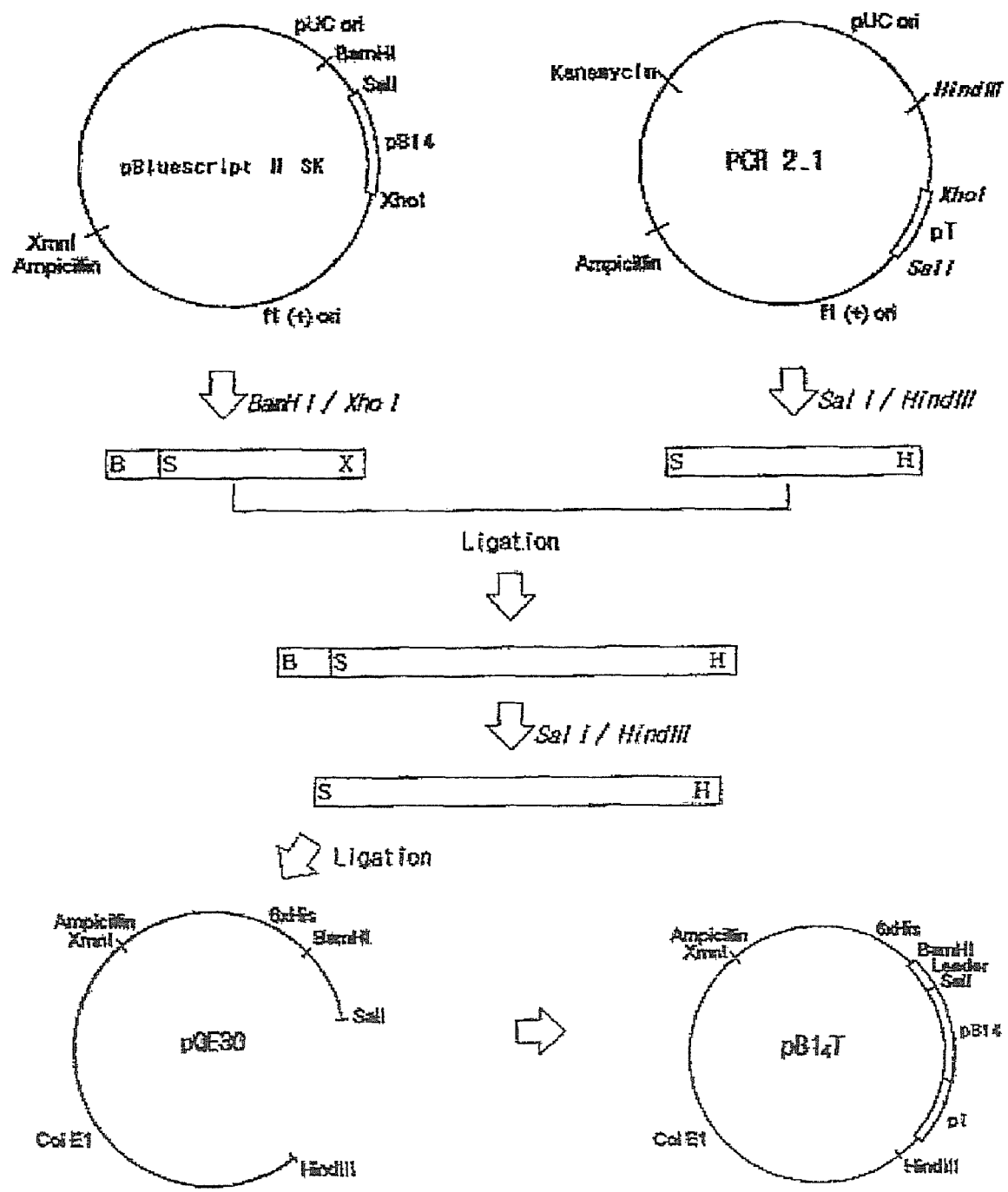
FIG. 1 shows a process of constructing $pB1_4T$.

In one aspect, the present invention relates to an immunogenic hybrid polypeptide, which comprises an amino acid sequence of a mimetic peptide of a B cell epitope of apolipoprotein B-100 and in which a C-terminus of the mimetic peptide is fused to an N-terminus of a helper T cell epitope.

In a strategy to enhance the immunogenicity of an apolipoprotein, the present invention intends to provide an immunogenic hybrid polypeptide in which a T cell epitope is fused to a mimetic peptide of a B cell epitope of an apolipoprotein, especially apolipoprotein B-100 (apo B-100). When a T cell epitope was fused to a mimetic peptide of the B cell epitope of apo B-100, $PB1_4$ had improved ability to induce antibody responses and displayed vaccine efficacy for an extended period of time, and so had an excellent anti-obesity effect.

The term "mimetic peptide of an epitope", as used herein refers to a peptide that mimics a minimal part of the epitope, which is an epitope that is sufficiently similar to a native epitope so that it can be recognized by an antibody specific to the native epitope, or that is able to increase an antibody to crosslink with a native epitope. A mimetic peptide is also called a mimotope. Such a mimetic peptide is advantageous because it is recognized as "non-self" in vivo and thus overcomes the problem of self-tolerance in immune responses. The mimetic peptide of a B cell epitope of apo B-100 is recognized by an antibody specifically binding to apo B-100. The antibody specifically binding to apo B-100 includes polyclonal and monoclonal antibodies, which specifically recognize and bind to apo B-100, and fragments thereof, for example, Fc, Fab and F(ab')2.

The mimetic peptide of a B cell epitope of apo B-100 according to the present invention includes an amino acid sequence selected from SEQ ID Nos. 1, 2 and 3. Thus, in a preferred aspect, the present invention relates to an immunogenic hybrid polypeptide, which includes an amino acid sequence selected from SEQ ID Nos. 1, 2 and 3, and in which a C-terminus of a peptide recognized by an antibody specifically binding to apo B-100 is fused to an N-terminus of a helper T cell epitope.

The present inventors isolated mimetic peptides (SEQ ID Nos. 1, 2 and 3) that are recognizable by a monoclonal antibody against apo B-100, Mab B9 or Mab B23, from a phage displayed peptide library by biopanning with the library.

The mimetic peptide of the epitope of apo B-100, which includes an amino acid sequence selected from SEQ ID Nos. 1, 2 and 3, may be in a monomeric form that is composed of a single copy of the amino acid sequence having any one of the SEQ ID Nos., or, to further enhance the immunogenicity of the mimetic peptide, may be in a multimeric form in which two or more, preferably three to eight, and more preferably three to six copies of the amino acid sequence having any one of the SEQ ID Nos. are linked. Most preferred is a tetramer (SEQ ID No. 4) in which four copies are linked. When the mimetic peptide is in a multimeric form, amino acid sequences each of which constitutes a monomer may be covalently linked directly or via a linker. When the amino acid sequences are linked via a linker, the linker may consist of one to five amino acid residues, which are selected from, for example, glycine, alanine, valine, leucine, isoleucine, proline, serine, threonine, asparagine, aspartic acid, cysteine, glutamine, glutamic acid, lysine and arginine. Preferred amino acids available in the linker may include valine, leucine, aspartic acid, glycine, alanine and proline. More preferably, taking the ease of gene manipulation into account, two amino acids selected from valine, leucine, aspartic acid, etc. may be linked and used as a linker. A preferred mimetic peptide is prepared by linking two or more copies of an amino acid sequence selected from SEQ ID Nos. 1, 2 and 3 via the linker.

The term "T cell epitope", as used herein, refers to an amino acid sequence that is able to bind to MHC Class II molecules with a suitable efficiency and stimulate T cells or bind to T cells in a complex with MHC Class II. In this case, the T cell epitope is recognized by a specific receptor present on T cells, and functions to provide a signal requiring the differentiation of B cells to antibody-producing cells and induce cytotoxic T lymphocytes (CTL) to destroy target cells. The T cell epitope is not specifically limited as long as it stimulates T cells and strengthens immune responses, and a variety of proteins, peptides, etc. suitable for the purpose are available. With respect to the objects of the present invention, the T cell epitope is preferably a helper T cell epitope. Examples of the helper T cell epitope may include hepatitis B surface antigen helper T cell epitopes, *Chlamydia trachomitis* major outer membrane protein helper T cell epitopes, *Plasmodium falciparum* circumsporozoite helper T cell epitopes, *Escherichia coli* TraT helper T cell epitopes, Tetanus toxoid helper T cell epitopes, diphtheria toxoid helper T cell epitopes, *Schistosoma mansoni* triose phosphate isomerase helper T cell epitopes, measles virus F protein helper T cell epitopes, T cell epitope sequences derived from pertussis vaccines, BCG (Bacile Calmette-Guerin), polio vaccines, mumps vaccines, rubella vaccines, rabies vaccines, purified protein derivatives of tuberculin, keyhole limpet hemocyanin, and fragments or combinations thereof. The T cell epitope may include an addition, deletion or substitution of a selected amino acid residue according to the specific purpose, and may be provided in a multimeric form in which two or more different T cell epitopes are linked. In an embodiment of the present invention, a surface antigen of hepatitis B virus is used. The genome of hepatitis B virus (HBV) is 3.2 kb in length, possesses the information for four important proteins and contains four open reading frames, S gene (surface antigen protein), C gene (core protein), P gene (DNA polymerase) and X gene. The S gene is divided into an S region encoding HBsAg and a preS region. The preS region is divided into preS1 encoding 108 or 119 amino acids according to HBV strains and preS2 encoding 55 amino acids regardless of subtype. The HBV preS2 protein activates helper T cells during in vivo immune responses, thereby stimulating the formation of an antibody against HBV.

The term "hybrid polypeptide", as used herein, generally indicates a peptide in which heterogenous peptides having different origins are linked, and in the present invention, refers to a peptide in which a B cell epitope and a T cell epitope are linked. This hybrid polypeptide may be obtained by chemical synthesis or expression and purification through genetic recombination after each partner is determined. Preferably, a hybrid gene, in which a gene sequence encoding a B cell epitope is linked to another gene sequence encoding a T cell epitope, is expressed in a cell expression system. In such a hybrid polypeptide, the B cell epitope and the T cell epitope may be linked directly or by means of a connector, such as a linker. When a linker is used, it should not negatively affect the induction of immune responses by the hybrid polypeptide.

The term "polypeptide", as used herein, is a term including a full-length amino acid chain in which residues including two or more amino acids are conjugated by covalent peptide bonds, and includes dipeptides, tripeptides, oligopeptides and polypeptides. In particular, in the present invention, the polypeptide means a hybrid polypeptide in which two or more peptides, in which several to several tens of amino acids are covalently bonded, are linked with each other. The hybrid polypeptide of the present invention is a polypeptide in which two or more peptides, for example, a B cell epitope and a T cell epitope, are linked. Each peptide sequence comprising the polypeptide includes a sequence corresponding to the aforementioned epitope, and may further include a sequence adjacent to the epitope. These peptides may be made of L- or D-amino acids, or may be in various combinations of amino acids in two different configurations. The hybrid polypeptide of the present invention may be entirely composed of an antigenic region including the aforementioned B cell epitope, T cell epitope and a certain sequence adjacent thereto, and may further include an additional sequence. However, this additional sequence preferably should not reduce the overall immunogenicity. Such an additional sequence is exemplified by a linker sequence.

The term "immunogenicity", as used herein, refers to the ability to induce both cellular and humoral immune responses to defend the body against impurities. A material inducing such immune responses is called an immunogen. The present invention employs a polypeptide having both a B cell epitope and a T cell epitope, which are immunogenic materials.

Figure 4:
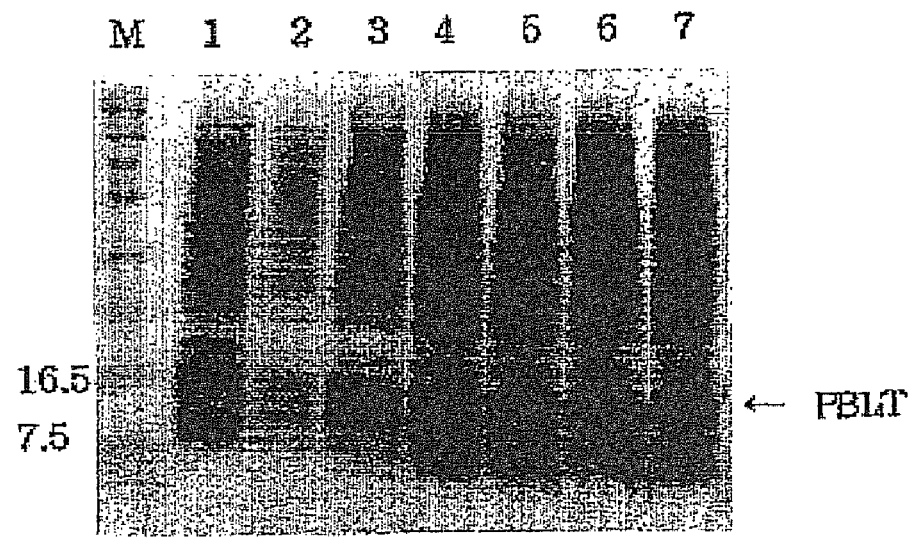
FIG. 4 shows the results of SDS-PAGE analysis for $PB1_4T$ expression in a transformed *Escherichia coli* strain, $M15/pB1_4T$, which has been treated with IPTG to induce $PB1_4T$ expression, wherein the expressed recombinant $PB1_4T$ is indicated by an arrow (M: prestained protein size marker; lane 1: *E. coli* M15 not induced with IPTG; and lanes 3 to 7: IPTG-induced *E. coli* $M15/pB1_4T$, collected 1, 2, 3, 4 and hrs, respectively, after IPTG induction)
Figure 5:
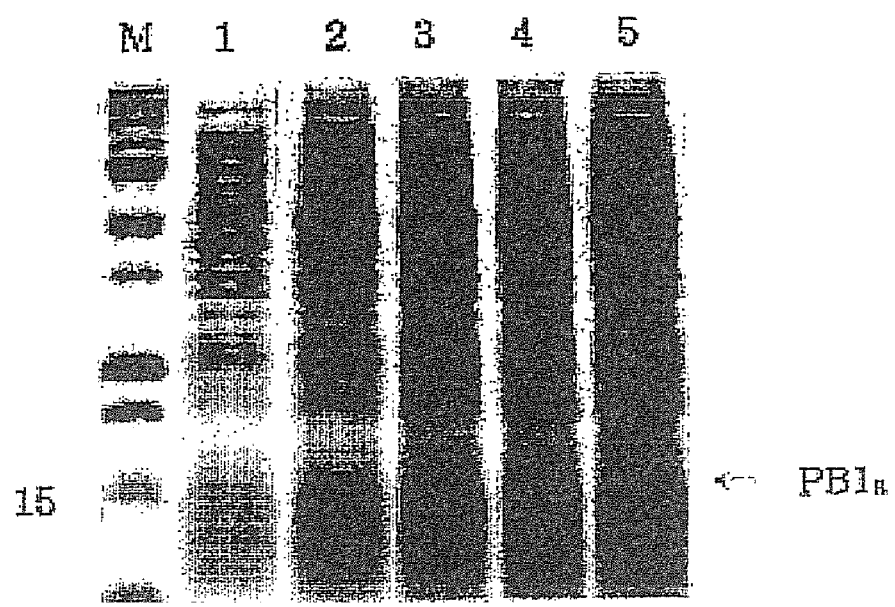
FIG. 5 shows the results of SDS-PAGE analysis for $PB1_8$ expression in a transformed *Escherichia coli* strain, $M15/pB1_8$, which has been treated with IPTG to induce $PB1_8$ expression, wherein the expressed recombinant $PB1_8$ is indicated by an arrow (M: prestained protein size marker; lane 1: *E. coli* M15 not induced with IPTG; and lanes 3 to 7: IPTG-induced *E. coli* $M15/pB1_8$, collected 1, 2, 3, 4 and 5 hrs, respectively, after IPTG induction)

The present inventors linked a C-terminus of $PB1_4$, which is a tetrameric apo B-100 mimetic peptide that is an anti-obesity functional peptide having a B cell epitope but deficient in a T cell epitope, to a portion (T fragment) of HBV preS2 having a T cell epitope, thereby generating a gene fragment for the expression of $PB1_4T$ (FIG. 1). A $PB1_4$ fragment was obtained using BamHI and XhoI, and a T fragment was obtained using SalI and HindIII. The $PB1_4T$ gene fragment was inserted into a pQE30 vector and transformed into *E. coli* JM109. An emerged colony was analyzed by restriction mapping (FIG. 2) and DNA sequencing (FIG. 3), and was found to be a correct clone in which the B cell epitope is linked to the T cell epitope. This clone was designated "$pB1_4T$". The pQE30 vector used for the expression of $PB1_4T$ and $PB1_8$ initiates protein expression from its internal start codon along with six histidine residues for the convenience of protein purification, followed by an enterokinase cleavage site. The thus expressed $PB1_4T$ is 16.2 kDa, and $PB1_8$ is 16.5 kDa. Protein expression was investigated by subjecting samples collected at given time points to SDS-PAGE analysis (FIGS. 4 and 5).

Thus, an immunogenic hybrid polypeptide of SEQ ID No. 9, in which a tetrameric apo B-100 mimetic peptide is linked to an HBV surface antigen preS2, may be provided in the practice of the present invention.

The immunogenic hybrid polypeptide of the present invention may be produced by chemical synthesis or genetic recombination. Preferably, the present hybrid polypeptide may be produced by transforming a host cell with a recombinant vector and isolating and purifying a polypeptide expressed by the host cell.

Thus, in another aspect, the present invention provides a recombinant vector comprising a gene encoding the immunogenic hybrid polypeptide, and a host cell transformed with the recombinant vector.

In a further aspect, the present invention provides a method of producing the immunogenic hybrid polypeptide by culturing a host cell transformed with the recombinant vector.

A process of producing the immunogenic hybrid polypeptide of the present invention by genetic recombination comprises the following four steps.

The first step is to insert a gene encoding the hybrid polypeptide into a vector to construct a recombinant vector. A vector into which foreign DNA is introduced may be a plasmid, a virus, a cosmid, or the like. The recombinant vector includes a cloning vector and an expression vector. A cloning vector contains a replication origin, for example, a replication origin of a plasmid, pharge or cosmid, which is a "replicon" at which the replication of an exogenous DNA fragment attached thereto is initiated. An expression vector was developed for use in protein synthesis. A recombinant vector serves as a carrier for a foreign DNA fragment inserted thereto, which typically means a double-stranded DNA fragment. The term "foreign DNA", as used herein, refers to DNA derived from a heterogeneous species, or a substantially modified form of native DNA from a homogenous species. Also, the foreign DNA includes a non-modified DNA sequence that is not expressed in cells under normal conditions. In this case, a foreign gene is a specific target nucleic acid to be transcribed, which encodes a polypeptide. The recombinant vector contains a target gene that is operably linked to transcription and translation expression regulatory sequences, which exert their functions in a selected host cell, in order to increase expression levels of the transfected gene in the host cell. The recombinant vector is a genetic construct that contains essential regulatory elements to which a gene insert is operably linked to be expressed in cells of an individual. Such a genetic construct is prepared using a standard recombinant DNA technique. The type of the recombinant vector is not specifically limited as long as the vector expresses a target gene in a variety of host cells including prokaryotes and eukaryotes and functions to produce a target protein. However, preferred is a vector which is capable of mass-producing a foreign protein in a form similar to a native form while possessing a strong promoter to achieve strong expression of the target protein. The recombinant vector preferably contains at least a promoter, a start codon, a gene encoding a target protein, a stop codon and a terminator. The recombinant vector may further suitably contain DNA coding a signal peptide, an enhancer sequence, 5'- and 3'-untranslational regions of a target gene, a selection marker region, a replication unit, or the like.

The second step is to transform a host cell with the recombinant vector and culture the host cell. The recombinant vector is introduced into a host cell to generate a transformant by a method described by Sambrook, J. et al., Molecular Cloning, A Laboratory Manual (2nd Ed.), Cold Spring Harbor Laboratory, 1. 74, 1989, the method including a calcium phosphate or calcium chloride/rubidium chloride method, electroporation, electroinjection, chemical treatments such as PEG treatment, and gene gun. A useful protein can be produced and isolated on large scale by culturing a transformant expressing the recombinant vector in a nutrient medium. Common media and culture conditions may be suitably selected according to host cells. Culture conditions, including temperature, pH of a medium and culture time, should be maintained suitable for cell growth and mass production of a protein of interest. Host cells capable of being transformed with the recombinant vector according to the present invention include both prokaryotes and eukaryotes. Host cells having high introduction efficiency of DNA and having high expression levels of an introduced DNA may be typically used. Examples of host cells include known prokaryotic and eukaryotic cells such as *Escherichia* sp., *Pseudomonas* sp., *Bacillus* sp., *Steptomyces* sp., fungi and yeast, insect cells such as *Spodoptera frugiperda* (Sf9), and animal cells such as CHO, COS 1, COS 7, BSC 1, BSC 40 and BMT 10. *E. coli* may be preferably used.

The third step is to induce the hybrid polypeptide to express and accumulate. In the present invention, the inducer IPTG was used for the induction of peptide expression, and induction time was adjusted to obtain maxmimal protein yield.

The final step is to isolate and purify the hybrid polypeptide. Typically, a recombinantly produced peptide can be recovered from a medium or a cell lysate. When the peptide is in a membrane-bound form, it may be liberated from the membrane using a suitable surfactant solution (e.g., Triton-X 100) or by enzymatic cleavage. Cells used in the expression of the hybrid peptide may be destroyed by a variety of physical or chemical means, such as repeated freezing and thawing, sonication, mechanical disruption or a cell disrupting agent, and the hybrid peptide may be isolated and purified by commonly used biochemical isolation techniques (Sambrook et al., Molecular Cloning: A laboratory Manual, 2nd Ed., Cold Spring Harbor Laboratory Press, 1989; Deuscher, M., Guide to Protein Purification Methods Enzymology, Vol. 182. Academic Press. Inc., San Diego, Calif., 1990). Non-limiting examples of the biochemical isolation techniques include electrophoresis, centrifugation, gel filtration, precipitation, dialysis, chromatography (ion-exchange chromatography, affinity chromatography, immunosorbent affinity chromatography, reverse phased HPLC, gel permeation HPLC), isoelectric focusing, and variations and combinations thereof.

In detail, in the present invention, the $PB1_4T$ gene fragment was ligated with a pQE30 vector and transformed into *E. coli*. The pQE30 vector is useful for mass-producing proteins in *E. coli* because it contains a promoter element consisting of the phage T5 promoter and a lac operator system using IPTG as an inducer. The expression of $PB1_4T$ was confirmed by Western blotting using two antibodies recognizing $PB1_4T$, a rabbit anti-PB14 polyclonal antibody and a mouse anti-preS2 monoclonal antibody, as primary antibodies, and expressed proteins were then purified. $PB1_4$ and $PB1_4T$ were denatured with 8 M urea because they are insoluble, and were purified by affinity chromatography using Ni-NTA resin for histidine-tagged proteins.

Rats were immunized with the expressed and purified polypeptide, and were assessed for an increase in body weight of rats, serum antibody titers and changes in serum lipid profiles. As a result, compared to a normal group or a group vaccinated with a non-fusion mimetic peptide, a group vaccinated with the hybrid polypeptide showed suppressed weight gain, high titers and extended retention of an antibody against the mimetic peptide, and decreased serum levels of TG and LDL-cholesterol.

There is no consistent rule applicable to peptide vaccine design, and the efficacy of designed vaccines is also unpredictable. For the same reasons, when a highly hydrophobic $PB1_4$ peptide is fused with a T cell epitope that is a heterogeneous peptide, an antigenic region can be internalized into the fusion protein, leading to a decrease in its ability to induce antibody responses. In this difficult situation to deduce the fusion results, the present inventors designed the hybrid polypeptide in which a mimetic peptide of the apo B-100 epitope is linked to a T cell epitope, and demonstrated that the hybrid polypeptide has increased immunogenicity that results in increased anti-obesity effect.

The immunogenicity of an artificially synthesized hybrid polypeptide and a vaccine comprising the same is achieved when a B cell epitope and a helper T cell epitope are present at the same time. Also, the efficacy of the vaccine may be determined according to the orientation of the B cell epitope and the helper T cell epitope. That is, the ability of the hybrid polypeptide to induce antibody responses may vary depending on the helper T cell epitope being located at an N-terminus or a C-terminus of the B cell epitope (Partidos, C, Stanley, C, and Steward, M, The effect of orientation of epitope on the immunogenicity of chimeric synthetic peptides representing measles virus protein sequences, Molecular Immunology, 29(5), 651-658, 1992).

In order to investigate the effect of the orientation of the B cell epitope and the helper T cell epitope on the induction of immune responses, the present inventors prepared a $TB1_4$ gene fragment by linking an N-terminus of $PB1_4$ to a T fragment (FIG. 12), unlike the preparation of the $B1_4T$ gene fragment involving linking a C-terminus of $PB1_4$ to a T fragment. In detail, a $pTB1_4$ vector was constructed according to a method described in Example 9, transformed into *E. coli* M15, and expressed therein. The expressed hybrid polypeptide $PTB1_4$, which has a His tag, was purified by affinity chromatography using Ni-NTA His-bound resin.

In order to compare $PTB1_4$ and $PB1_4T$ for their ability to induce antibody responses and immunogenicity, SD rats were immunized with each of the polypeptides, and blood samples were collected. Compared to $PB1_4$, $PTB1_4$ had enhanced ability to induce antibody responses, and the retention period of the serum antibody against $PTB1_4$ was prolonged. However, these improvements upon immunization with $PTB1_4$ were remarkably found to be about 50-60% lower than with $PB1_4T$ (FIG. 16). The same results were found in the suppression of body weight gain of the rats (Table 2). These results indicate that the $PB1_4T$ polypeptide, prepared by linking a C-terminus of $PB1_4$ to a T fragment, has much stronger immunogenicity and anti-obesity effects.

Thus, in yet another aspect, the present invention relates to a vaccine for preventing or treating obesity, comprising an immunogenic hybrid polypeptide which includes an amino acid sequence of a mimetic peptide of the apo B-100 epitope and in which a C-terminus of the mimetic peptide is fused to an N-terminus of a helper T cell epitope.

An immunogen can be determined to be available as a vaccine having good efficacy by comparing the magnitude of responses to the immunogen and the ratio of observed individuals. In the present invention, with respect to the present object to provide a vaccine for preventing and treating obesity, the effect of an antigen on the induction of immune responses was assessed by investigating (a) body weight gain, (b) serum antibody titers and (c) changes in serum lipid profiles, thereby determining a highly efficient form of the antigen.

In detail, 100 μg of each of purified $PB1_4$ and $PB1_4T$ peptides were intraperitoneally injected into 7-week-old SD white rats three times at 2-week intervals, and changes in body weight of the rats were observed and plotted on a graph (FIG. 15). From the primary injection to boosting (secondary injection), rats of each group showed similar body weight ranging from 292 g to 297 g. However, from one week after the secondary injection, a difference in body weight of rats was observed between vaccinated groups and normal and mock groups. This indicates that the weak immune responses induced by the primary injection were enhanced after boosting by the secondary injection, and that the enhanced immune responses lead to the suppression of body weight gain of rats. Compared to the normal and mock groups, the vaccinated groups displayed a reduction in body weight increment. Also, the $PB1_4T$ peptide had a stronger inhibitory effect on body weight increment than the $PB1_4$ peptide (Table 2). This difference in body weight increment was maintained even after the third injection. In addition, the chimeric antigen $PB1_4T$, which was homogenous, was found to more effectively induce immune responses than the $PB1_4$ peptide conjugated with a carrier protein, ovalbumin. In vaccinated SD white rats, serum antibody titers were measured at 10, 12, 14 and 16 weeks of age by ELISA (FIG. 16). The $PB1_4T$-immunized group showed increased antibody titers relative to the $PB1_4$-immunized group. At 14 weeks of age, the $PB1_4T$-immunized group displayed 1.5-fold higher absorbancy (O.D.: optical density) values than the $PB1_4$-immunized group. At 16 weeks of age, the $PB1_4$-immunized group showed a reduction in antibody titer, whereas the $PB1_4T$-immunized group maintained the increased antibody titers. With respect to serum lipids, the vaccinated groups displayed lower levels of TG and cholesterol than the normal and mock groups. In particular, LDL-cholesterol levels were reduced to 60% of normal levels (FIG. 17).

These results demonstrate that a fusion form of $PB1_4$ with a T cell epitope has higher immunogenicity than $PB1_4$ itself, which has a B cell epitope, and thus can be used in an effective vaccine composition.

In addition, the present inventors conducted a clinical test with pet dog subjects for the efficacy of $PB1_4T$. $PB1_4T$ was mixed with alumina and injected into ten pet dogs twice at 2-week intervals, and changes in body weight were observed. As a result, no increment in body weight was found in the pet dogs even when the dogs were allow to freely eat snacks and high-fat diets (Table 4). Also, when serum samples were collected from the immunized pet dogs after the secondary injection and serum antibody titers were measured by ELISA, high absorbance was found even when the serum samples were diluted 5,000-50,000 times, indicating that the $PB1_4T$ peptide has an excellent effect on the induction of antibody responses.

The anti-obesity vaccine of the present invention is composed of an antigen, a pharmaceutically acceptable carrier, a suitable adjuvant and other common materials, and is administered in an immunologically effective amount. The term "immunologically effective amount", as used herein, refers to an amount that is sufficient to exert the therapeutic and preventive effect on obesity and does not cause side effects or severe or excess immune responses. An accurate dosage may vary according to the specific immunogen to be administered, and may be determined by those skilled in the art using a known method for assaying the development of an immune response. Also, the dosage may vary depending on administration forms and routes, the recipient's age, health state and weight, properties and degree of symptoms, types of currently received therapy, and treatment frequency. The carriers are known in the art and include a stabilizer, a diluent and a buffer. Suitable stabilizers include carbohydrates, such as sorbitol, lactose, mannitol, starch, sucrose, dextran and glucose, and proteins, such as albumin or casein. Suitable diluents include saline, Hanks' Balanced Salts and Ringer's solution. Suitable buffers include an alkali metal phosphate, an alkali metal carbonate and an alkali earth metal carbonate. The vaccine may also contain one or more adjuvants to enhance or strengthen immune responses. Suitable adjuvants include peptides; aluminum hydroxide; aluminum phosphate; aluminum oxide; and a composition that consists of a mineral oil, such as Marcol 52, or a vegetable oil and one or more emulsifying agents, or surface active substances such as lysolecithin, polycations and polyanions. The vaccine composition of the present invention may be administered as an individual therapeutic agent or in combination with another therapeutic agent, and may be co-administered either sequentially or simultaneously with a conventional therapeutic agent. The vaccine composition may be administered via known administration routes. Administration methods include, but are not limited to, oral, intradermal, intramuscular, intraperitoneal, intravenous, subcutaneous, and intranasal routes. Also, a pharmaceutical composition may be administered using a certain apparatus, which can deliver an active material to target cells.

A better understanding of the present invention may be obtained through the following examples which are set forth to illustrate, but are not to be construed as the limit of the present invention.

EXAMPLES

Test Materials

A DNA miniprep kit and a kit used to extract DNA from a gel were purchased from Nucleogen, Bacto trypton, Bacto yeast extract, agar, etc. from Difco (Detroti, Mich.), restriction enzymes from Takara, and T4 DNA ligase from NEB. pBluescript II SK (Stratagene), PCR 2.1 (Invitrogen, Carlsbad, Calif.) and pQE30 (Qiagen) vectors and $E.$ $coli$ JM109 and M15 strains (Qiagen) were used.

IPTG used to induce protein production was purchased from Sigma, the Ni-NTA resin used to purify expressed proteins from Novagen, and the prestained marker used in SDS-PAGE, Western blotting, ECL, etc. from NEB. Urea used to denature proteins was purchased from Duchefa, and immidazole used in protein purification from USB. The membrane used in dialysis was MWCO 3,500 purchased from Spectrum, and the reagent used to prevent protein aggregation was CHAPS from Amresco. The antibody used in ELISA was HRP-conjugated anti-rat IgG from Sigma. The substrate solution used in Western blotting and ECL was BCIP/NBT from Sigma, and the ECL Plus Western Blotting Detection Reagent was purchased from Amersham. Adjuvants used were Freund's adjuvant (Sigma) and aluminum hydroxide (Reheis). Protein concentration was determined by Pierce's BCA protein assay and Biorad's Bradford assay.

Tryglycerides, total cholesterol, HDL cholesterol and LDL cholesterol in the serum were measured using triglyzyme-V, cholestezyme-V, HDL-C555 (Shinyang Diagnostics, Korea) and EZ LDL cholesterol (Sigma), respectively. An LDL calibrator (Randox) was used.

5-week-old male Sprague Dawley (SD) white rats were purchased from Daehan Biolink Co. Ltd., Korea, and fed with a feedstuff from Samtako Inc., Korea, which contains more than 18% natural proteins, 5.3% crude fats, 4.5% crude fiber and 8.0% ash.

The following buffers were used to purify recombinant $PB1_4T$ and $PB1_4$ peptides: sonication disruption buffer (5 mM imidazole, 0.5 M NaCl, 20 mM Tris-Cl, pH 7.9), binding buffer (5 mM imidazole, 0.5 M NaCl, 20 mM Tris-Cl, 8 M urea, pH 7.9), washing buffer (50 mM imidazole, 0.5 M NaCl, 20 mM Tris-Cl, 8 M urea, pH 7.9), and elution buffer (400 mM imidazole, 0.5 M NaCl, 20 mM Tris-Cl, 8 M urea, pH 7.9).

Example 1

Preparation of an Artificial Gene for Production of anti-obesity $PB1_4T$ peptide A pBluescript II SK vector was digested with BamHI and XhoI to obtain a $B1_4$ fragment, and a PCR 2.1 vector was digested with SalI and HindIII to obtain a T fragment. Since XhoI and SalI have compatible cohesive ends, the $B1_4$ and T fragments, obtained from the two vectors, were ligated using T4 DNA ligase at 16° C. for 12 hrs. Since the ligated site is not digested by SalI or XhoI, SalI/HindIII digestion was carried out again to obtain a $B1_4T$ fragment. For protein expression, a pQE30 plasmid was selected as a vector system, which is designed to express a protein of interest in a form fused with six histidine residues to facilitate protein purification. The $B1_4T$ gene fragment was inserted into SalI/HindIII sites of the pQE30 vector. The resulting expression vector was designated "$pB1_4T$" (FIG. 1). The expression vector was transformed into *E. coli* JM109. Plasmid DNA was isolated from the transformed cells and subjected to restriction mapping with SalI and HindIII. As a result, a 450 bp fragment was successfully inserted into the pQE30 vector (FIG. 2).

The recombinant vector $pB1_4T$ was deposited in the form of being transformed into *E. coli* (*E. coli* M15/$pB1_4T$) at the Korean Culture Center of Microorganisms (KCCM, 361-221, Yurim B/D, Honje 1-dong, Sudaemum-gu, Seoul, Republic of Korea) on Mar. 4, 2004, and was assigned accession number KCCM-10562.

Example 2

Preparation of an Artificial Gene for Production of Anti-Obesity $PB1_8$ Peptide A pBluescript II SK vector was digested with Sail and XhoI to obtain a $B1_4$ fragment. A pBX4 vector (pQE30 vector having a $B1_4$ fragment insert, Korean Pat. Laid-open Publication No. 2002-0018971) was linearlized by Sail digestion, and ligated with the $B1_4$ fragment using T4 DNA ligase at 16° C. overnight.

Example 3

Nucleotide Sequence Determination of Gene

In order to confirm whether the BIZ gene fragment is correctly inserted in the $pB1_4T$ recombinant vector, the recombinant vector was prepared in a concentration of 300-500 ng/μg and subjected to DNA sequencing, which was performed by Core Bio System Co. Ltd., Korea. As a result, the selected recombinant vector was found to be a correct clone (FIG. 3).

Example 4

Recombinant Peptide $PB1_4T$ Expression

The $PB1_4T$ and $PB1_8$ peptides were expressed from the pQE30 vector, which initiates protein expression from its internal start codon along with six histidine residues for convenience of protein purification, followed by an enterokinase cleavage site. *E. coli* M15 was used as a host cell for peptide expression. The *E. coli* M15 strain was transformed with a recombinant vector and smeared onto LB plates containing ampicillin (Amp) and kanamycin (Kan). An emerged colony was cultured in 10 ml of LB medium containing Amp (100 µg/ml) and Kan (25 µg/ml) overnight. In order to investigate protein expression according to culture time, 1 ml of the overnight-cultured culture was inoculated in 50 ml of fresh LB medium. Then, the cells were incubated with agitation at 37° C. for 1 hr 30 min, where OD at 600 nm was 0.4 to 0.5. At this state, IPTG was added to the medium at a final concentration of 1 mM, and the cells were further cultured for 5 hrs, during which 1 ml of the culture was collected every hour. Before IPTG addition, 1 ml of the culture was collected to be used as a non-induced control. The collected samples were centrifuged at 14,000 rpm for 1 min. The cell pellets were dissolved in 30 µl of 2× SDS sample buffer and subjected to SDS-PAGE. The results are given in FIGS. 4 and 5. The SDS-PAGE analysis revealed that $PB1_4T$ is 16.2 kDa and $PB1_8$ is 16.5 kDa.

Example 5

Western Blotting for the Recombinant Peptide $PB1_4T$

The $PB1_4T$ peptide was identified by size analysis using SDS-PAGE, but in order to further confirm whether the expressed protein is $PB1_4T$, Western blotting was carried out using two antibodies capable of recognizing $PB1_4T$. As a control in Western blotting for $PB1_4T$, *E. coli* M15 was transformed with the pQE30 vector not containing the $B1_4T$ fragment. Samples were collected before IPTG induction and three hours after IPTG induction. A rabbit anti-$PB1_4$ polyclonal antibody and a mouse anti-preS2 monoclonal antibody were 1:10000 diluted in PBS and used as primary antibodies. As secondary antibodies capable of recognizing the primary antibodies, peroxidase-conjugated goat anti-rabbit IgG and goat anti-mouse IgG were used after being 1:10000 diluted in PBS. A resulting blot was developed using an ECL Plus Western Blotting Kit. The blot was placed in a cassette, and a sheet of Fuji medical X-ray film was placed onto the blot. The blot was exposed to the film for 10 sec and developed. Since the rabbit anti-$PB1_4$ polyclonal antibody recognizes a $PB1_4$ fragment of $PB1_4T$ and the mouse anti-preS2 monoclonal antibody recognizes a T fragment of $PB1_4T$, bands should be observed on both blots, which were individually incubated with each of the primary antibodies, when the $PB1_4T$ protein is correctly expressed. As shown in FIG. 8, the primary antibodies individually recognized $PB1_4$ and T of $PB1_4T$, indicating that $PB1_4T$ is correctly expressed.

Example 6

Evaluation of Expression Form of $PB1_4T$ and $PB1_8$ Recombinant Peptides in *E. coli*

Figure 6:
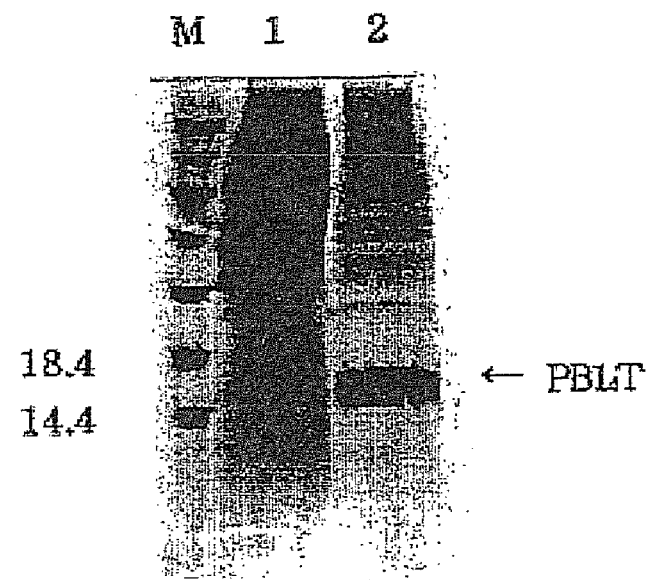
FIG. 6 shows the results of SDS-PAGE analysis of the centrifugal supernatant (lane 1) and pellet (lane 2) of an *E. coli* lysate, wherein expressed $PB1_4T$ is indicated by an arrow and is found in the pellet.
Figure 7:
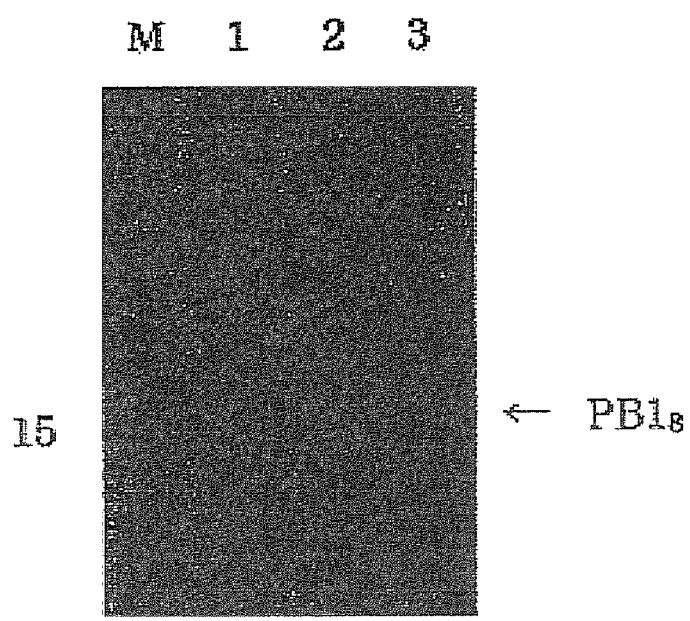
FIG. 7 shows the results of SDS-PAGE analysis of an *E. coli* lysate (lane 1: whole lysate; lane 2: centrifugal supernatant; lane 3: centrifugal pellet), wherein expressed $PB1_8$ is indicated by an arrow and is found in the pellet.

In order to determine whether $PB1_4T$ and $PB1_8$ were expressed as soluble or insoluble proteins, the cells were harvested three hours after IPTG induction by centrifugation. The harvested cells were resuspended in sonication buffer and sonicated. The resulting pellet and supernatant were analyzed by SDS-PAGE. In detail, the cells treated with IPTG to induce protein expression were centrifuged at 9,000 rpm at 4° C. for 30 min. The pelleted cells was frozen at −20° C. for a while, thawed on ice, and resuspended in sonication disruption buffer (5 ml per 1 g pellet). The cells were sonicated fifteen times for 30 sec (each time with 1 min pause). The cell lysate was then centrifuged at 9,000 rpm at 4° C. for 30 min. The supernatant was recovered, thus yielding a crude extract A containing unprocessed soluble proteins. Also, the pellet was recovered, thus giving a crude extract B containing unprocessed insoluble proteins. The crude extracts A and B were individually mixed with 2× SDS sample buffer, boiled at 95° C. for 5 min, and electrophoresed on an SDS-PAGE gel. The SDS-PAGE analysis revealed that the target proteins were present mainly in the pellet rather than the supernatant, indicating that the $PB1_4T$ and $PB1_8$ proteins are expressed in an insoluble form (FIGS. 6 and 7).

Example 7

Purification of $PB1_4$, $PB1_4T$ and $PB1_8$ Recombinant Peptides

Peptide purification was carried out using Ni-NTA resin for histidine-tagged proteins. This purification is an affinity chromatographic method using the interaction between $Ni^+$ bound to the resin and the histidine hexamer at a terminal end of a fusion protein. After transformed *E. coli* cells were pre-cultured in 10 ml of LB medium overnight, the 10-ml culture was inoculated in 500 ml of LB medium and cultured at 37° C. until OD at 600 nm reached 0.4 to 0.5. Then, 1 mM IPTG was added to the medium, and the cells were further cultured for 4 hrs. The cells were centrifuged at 9000 rpm for 30 min, and the cell pellet was placed at −20° C. After the frozen cells were thawed on ice, they were resuspended in sonication disruption buffer (5 ml/g of wet cells) and sonicated. The cell lysate was then centrifuged at 9000 rpm at 4° C. for 30 min. The pellet was resuspended in a volume of binding buffer equal to that of the supernatant, sonicated three times to remove cell debris, and centrifuged at 9000 rpm at 4° C. for 30 min. The thus obtained supernatant was subjected to affinity chromatography using Ni-NTA resin.

A column was 1 cm in diameter and 15 cm in height and was packed with 2 ml of a resin, and all of the steps were carried out at a flow rate of 2 ml/min. After the resin was packed into the column, the resin was washed with a three to five column volume of distilled water, and the resin was charged with $Ni^{2+}$ using a five column volume of 1× charge buffer (50 mM $NiSO_4$) and equilibrated with the binding buffer, thereby generating a Ni-chelate affinity column. After a sample was loaded onto the column twice, the column was washed with the binding buffer until the absorbance at 280 nm reached a baseline of 1.0 and then with washing buffer for 10 min. After the column was completely equilibrated, the column was eluted with elution buffer containing a higher concentration of imidazole than the washing buffer, thereby forming an imidazole gradient, and the elution was run alone through the column for a further 10 min to completely elute proteins bound to the resin. A total of twenty 2-ml fractions were collected. Since the eluted peptide was dissolved in 8 M urea, it was dialyzed in PBS overnight to remove urea.

Figure 10:
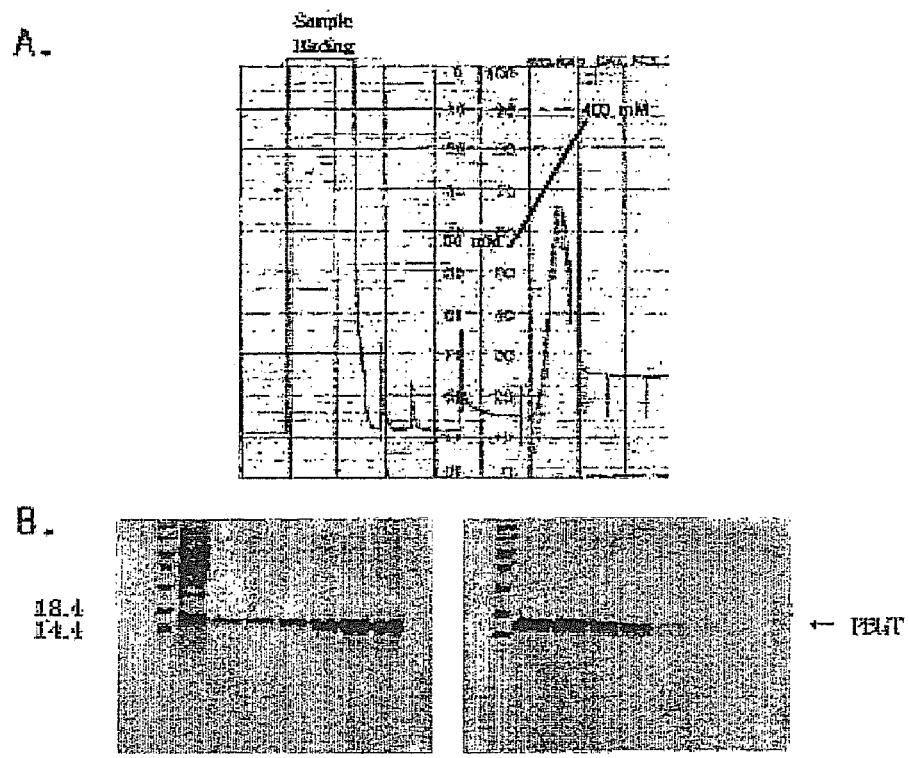
FIG. 10 shows the $PB1_4T$ elution profile resulting from Ni-NTA affinity chromatography according to a linear imidazole gradient.
Figure 11:
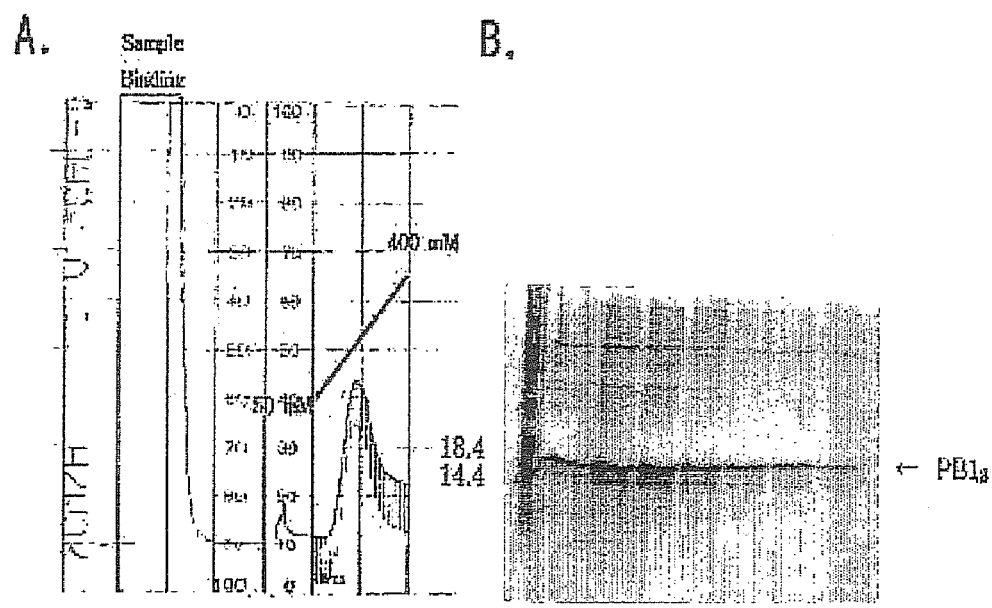
FIG. 11 shows the $PB1_8$ elution profile resulting from Ni-NTA affinity chromatography according to a linear imidazole gradient.
Figure 12:
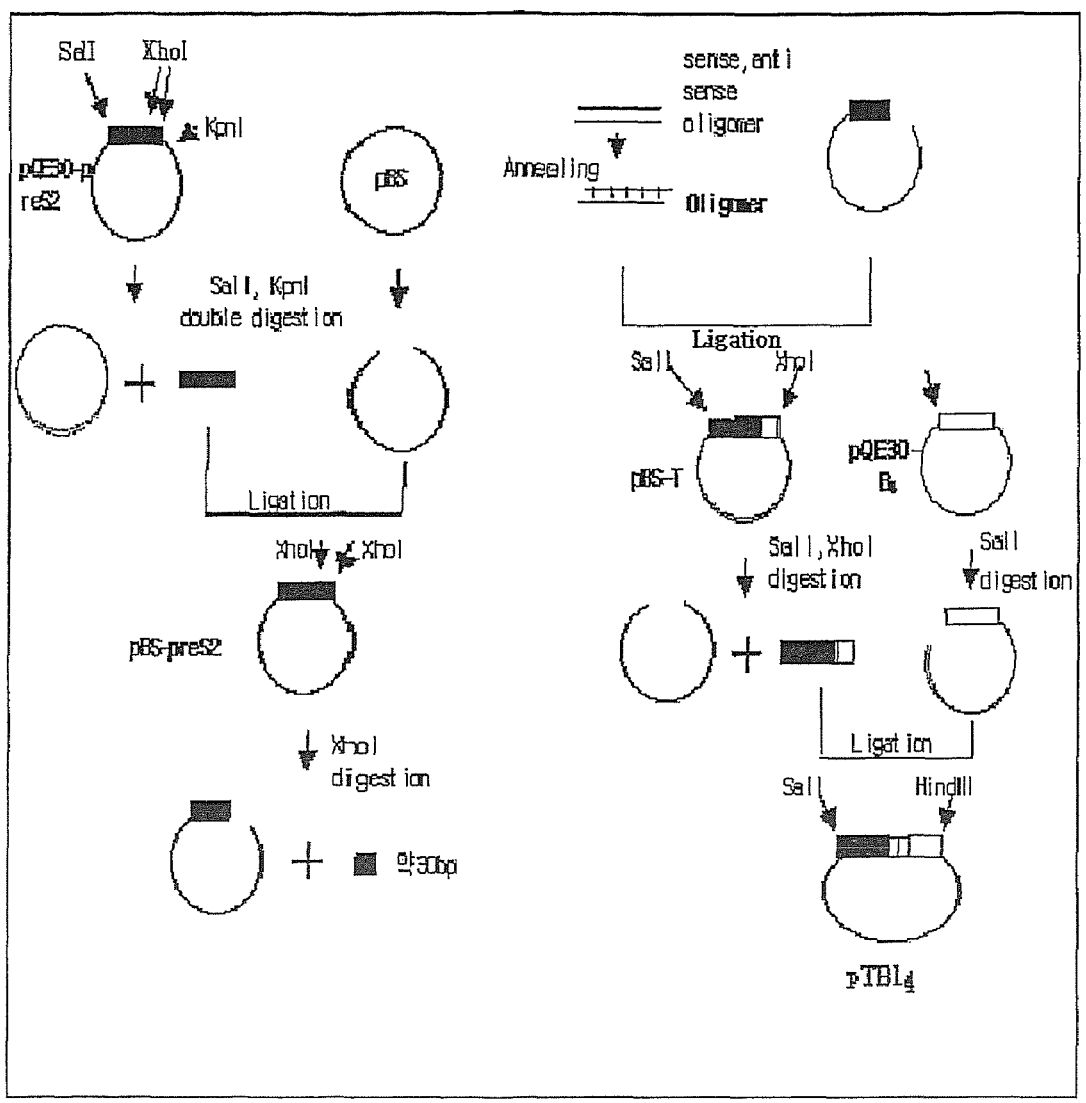
FIG. 12 shows a process of constructing $pTB1_4$.

As described above, since each protein was highly insoluble, it was purified after being denatured with a buffer containing 8 M urea, and proteins bound to the resin were eluted using an imidazole gradient of 50 mM to 400 mM. The results are given in FIGS. 9, 10 and 11. Most proteins were eluted at about 300 mM of imidazole. Protein yields per 1 L culture were 3-3.5 mg for $PB1_8$ and 4-4.5 mg for $PB1_4T$.

Example 8

Quantification of $PB1_4$, $PB1_4T$ and $PB1_8$ Recombinant Peptides

When the eluted $PB1_4T$, $PB1_4$ and $PB1_8$ peptides were dialyzed in PBS, proteins were aggregated because urea was removed, thus forming precipitates. In this state, accurate protein concentrations could not be measured. The aggregation of the purified proteins was solved using 50 mM CHAPS. Protein concentrations were determined by a BCA protein assay and a Bradford assay. 2 mg/ml of BSA was serially diluted to 1000, 500, 250, 125 and 62.5 µg/ml, and the serial BSA dilutions were used as standard. The BCA assay was performed according to the protocol provided by Pierce. The BCA protein color reaction was carried out at 37° C. for 30 min, and absorbance was then measured at 562 nm. Also, a sample was allowed to react with a Bradford reagent at room temperature for 10 min, and absorbance was then measured at 595 nm. Standard curves were obtained using the absorbance of serial dilutions of BSA or Bradford protein color reactions, and protein concentrations of samples were determined using the standard curves.

Example 9

Construction of $pTB1_4$ Vector for $PTB1_4$ Expression

The pQE30 vector, transformed into *E. coli* M15, was double-digested with KpnI (Takara) and SalI (Takara) to excise a T cassette (preS2). A pBluescript plasmid was also treated with the same restriction enzymes. The excised T cassette and linearlized pBluescript were separated on a gel, purified, and ligated with each other using T4 DNA ligase. 4 µl of pBluescript, 4 µl of T cassette, 1 µl of T4 DNA ligase (MBI Fermentas, 1 Weiss u/ml) and 1 µl of 10× buffer (MBI Fermentas) were mixed in a 1.5-ml tube, and the ligation mixture was incubated at 16° C. overnight. The recombined vector was then mixed with JM109 competent cells, heat-shocked at 42° C. for 90 sec, and incubated in LB medium at 37° C. for 1 hr. Then, the transformed cells were smeared onto LB/Amp plates and incubated at 37° C. Several colonies were randomly selected from the emerged colonies and cultured. Plasmid DNA was then isolated from the cultured cells, digested with restriction enzymes, and electrophoresed on an agarose gel to analyze the size of DNA fragments. An XhoI site in the T cassette was removed to obtain a $TB_4$ cassette. That is, since the T cassette (HBV preS2 gene, 183 bp) could not be used in cloning due to the XhoI site near its 3'-end (about 150 bp apart from the 5'-end of the T cassette), the T cassette was point-mutated at the internal XhoI site and thus had a new sequence. A short DNA fragment (30 bp) was excised from pBluescript-preS2 due to the internal XhoI site of the T cassette. Synthetic oligomers were inserted into this position. To prevent self-ligation, the vector was treated with alkaline phosphatase (Boehringer Mannheim, GmbH, Germany) at 37° C. for 30 min, dephosphorylated at 95° C. for 5 min, and eluted from a gel. The oligomers were phosphorylated at their 5'-ends by treatment with polynucleotide kinase at 37° C. for 30 min and 65° C. for 20 min. Then, the vector and the oligomers were allowed to stand at 95° C. for 5 min, and were slowly cooled in a heat block to be annealed. The oligomers and pBluescript-T were then treated with ligase at 16° C. overnight. The recombined pBluescript-T was transformed into JM109 cells and smeared onto LB/Amp plates.

After plasmid DNA was isolated from emerged colonies and analyzed, a clone carrying a desired plasmid was obtained. The oligomers consisted of 28 nucleotides corresponding to preS2, in which the fifth nucleotide, G, at the 5'-end of a sense-strand was replaced with A to remove XhoI site, thereby having a lysine substitution for arginine. Sense and anti-sense strands, each of which was designed to be 28 mer, were annealed and inserted into the XhoI-treated pBluescript-preS2. After the pBluescript-T was double-digested with SalI and XhoI and $pQE30-B_4$ was digested with SalI, they were purified from gels. The obtained T was inserted into the $pQE30-B_4$ cleaved at its 5'-end, thereby generating $pQE30-pTB_4$. The recombined $TB_4$ was confirmed by restriction mapping with SalI and HindIII. The thus obtained vector was designated $pTB1_4$ (FIG. 13).

Example 10

Expression and Purification of $PTB1_4$

The expression vector $pTB1_4$ was introduced into *E. coli* M15, and the transformed cells were cultured in 2 L of LB medium containing Amp and Kan. The cultured cells were centrifuged at 7000 rpm for 10 min, thus yielding 9 g of wet cells. Since the recombinantly expressed hybrid polypeptide $PTB_4$ had a His-tag, it was subjected to affinity chromatography using an Ni-NTA His-bound resin. A column used was 4 ml in resin volume, 1.8 cm in diameter and 8 cm in height. The absorbance range of an Econo system was 0.5, the paper speed of a recorder was 2 cm/hr, and the sample loading rate was 2 ml/min. First, the wet cells were suspended in sonication buffer, sonicated and centrifuged at 10,000 rpm at 4° C. for 30 min. The pellet was dissolved in binding buffer and subjected to affinity chromatography. A binding solution flowed through the column to settle a resin. When a baseline was decided using a detector and a predetermined value was indicated, the sonicated sample was loaded onto the column. When the sample entered into the column and a predetermined value was indicated, a washing solution was run through the column. When a predetermined value was indicated, an elution solution was run through the column, thereby isolating $PTB1_4$. The expressed and purified hybrid polypeptide was analyzed by SDS-PAGE and Western blotting. The $PTB1_4$ separated on an SDS-PAGE gel was transferred onto a membrane by semi-dry transfer. The blot was incubated in blocking buffer (0.5% casein-phosphate buffered saline-Tween, 0.02% $NaN_3$) at 37° C. for hrs, and washed with Tris-buffered saline-Tween (TBS-T, pH 7.6) twice for 2 min each washing. Then, the blot was incubated in a primary antibody at 37° C. for 1 hr and washed with TBS-T four times for 5 min each time. The blot was incubated in a secondary antibody for 1 hr and washed according to the same method. To identify the T cassette, an anti-preS2 monoclonal antibody (1:10,000) and an HRP-conjugated goat anti-mouse IgG antibody (1:10,000) were used. A B cassette was detected using a rabbit anti-$PB1_4$ anti-serum (1:10,000) and an HRP-conjugated goat anti-rabbit IgG antibody (1:10,000). After being dried, the blot was treated with ECL reagents for 5 min to detect bands. As a result, in the B cassette, which was detected using the rabbit anti-$PB1_4$ anti-serum and the HRP-conjugated goat anti-rabbit IgG antibody, an about 16-kDa band was found in $PB1_4T$ and $PTB1_4$ samples. In the T cassette, which was detected using the anti-preS2 monoclonal antibody and the HRP-conjugated goat anti-mouse IgG antibody, a band of about 8 kDa was found in the $PB1_4$ sample, and a band of about 16 kDa band was found in $PB1_4T$ and PTBl$_4$ samples. These results indicate that each hybrid polypeptide was accurately expressed and purified (FIG. 13).

Example 11

Conjugation of PBl$_4$ and Ovalbumin

PBl$_4$ was conjugated with a carrier protein, ovalbumin. The carrier protein and PBl$_4$ were mixed at a molar ratio of about 1:10, and allowed to react with agitation at 4° C. for about 1 hr in a reaction vial. After the reaction mixture was supplemented with 2% glutaraldehyde, it was allowed to react for 3 hrs. The reaction mixture was then dialyzed using a dialysis membrane, MWCO 3,000, in PBS buffer overnight to remove remaining glutaraldehyde.

Example 12

Vaccination (Immunization)

7-week-old SD white rats were divided into six groups and vaccinated (Table 1). As described in Table 1, 100 μg of each peptide, purified and quantified in Examples 7 and 10, was mixed with each adjuvant to give a final volume of 100 μl, and intraperitoneally injected into the rats. Injection was carried out three times at 2-week intervals, that is, at 7, 9 and 11 weeks of age. Freund's adjuvant and aluminum hydroxide were as adjuvants. The Freund's adjuvant was used in the same amount as the peptide. Aluminum hydroxide of 5.8 mg/ml was adjusted to a final concentration of 0.2 mg/ml, mixed with each peptide, and incubated with agitation at room temperature. Blood samples were collected five days after the first boosting and five days, two weeks and four weeks after the second boosting.

TABLE 2

Changes in body weight of SD rats after vaccination

| Age (wk) | Normal | Mock | PBl$_4$$^{+OVA}$ | PBl$_4$T | PTBl$_4$ |
|---|---|---|---|---|---|
| 6 | 130 ± 0 | 130 ± 0 | 130 ± 0 | 130 ± 0 | 130 ± 0 |
| 7$_{(V1)}$ | 200 ± 0 | 193 ± 6 | 202 ± 4 | 202 ± 4 | 201 ± 6 |
| 8 | 253 ± 6 | 257 ± 6 | 254 ± 9 | 254 ± 11 | 252 ± 5 |
| 9$_{(V2)}$ | 292 ± 8 | 299 ± 6 | 297 ± 13 | 303 ± 6 | 300 ± 8 |
| 10 | 325 ± 8 | 328 ± 4 | 323 ± 12 | 332 ± 7 | 332 ± 4 |
| 11$_{(V3)}$ | 354 ± 6 | 362 ± 3 | 357 ± 14 | 362 ± 10 | 359 ± 8 |
| 12 | 372 ± 15 | 376 ± 8 | 365 ± 11 | 362 ± 13 | 363 ± 13 |
| 13 | 395 ± 12 | 396 ± 12 | 383 ± 10 | 377 ± 13 | 379 ± 15 |
| 14 | 407 ± 14 | 407 ± 8 | 395 ± 8 | 391 ± 12 | 396 ± 10 |
| 15 | 413 ± 16 | 414 ± 9 | 403 ± 11 | 397 ± 10 | 401 ± 10 |
| 16 | 422 ± 18 | 424 ± 10 | 414 ± 13 | 406 ± 10 | 412 ± 10 |
| 17 | 436 ± 22 | 435 ± 11 | 425 ± 14 | 415 ± 9 | 420 ± 9 |
| 18 | 456 ± 24 | 452 ± 11 | 436 ± 12 | 425 ± 9 | 433 ± 11 |

In Table 2, all data are represented as mean±SD, wherein SD (standard deviation) was calculated for five SD white rats, and units are grams.

Example 13

Measurement of Antibody Titers

Antibody titers were measured using serum samples by indirect ELISA. 100 μl (100 ng) of PBl$_4$ was placed into each well of a microtiter plate. The plate was incubated at 4° C. overnight, and incubated in a blocking solution (PBS, 0.5% casein, 0.02% NaN$_3$) at 37° C. for 1 hr. Each well was washed with PBST three times. Serum samples collected from vaccinated SD rats were 1:500 to 1:8000 diluted in PBS. 100 μl of each diluted serum sample was added to each well, and incu-

TABLE 1

Vaccination with peptides

| | | | Test groups | | | | |
|---|---|---|---|---|---|---|---|
| | Normal | Mock | A | C | B | D | E |
| Antigen | PBS | OVA | PBl$_4$$^{(+OVA)}$ | PBl$_4$T | PBL$_4$$^{(-OVA)}$ | PBl$_8$ | PTBl$_4$ |
| Adjuvant | | Aluminum hydroxide | Freund's adjuvant or aluminum hydroxide | Freund's adjuvant or aluminum hydroxide | Aluminum hydroxide | Aluminum hydroxide | Freund's adjuvant or aluminum hydroxide |

Figure 15:
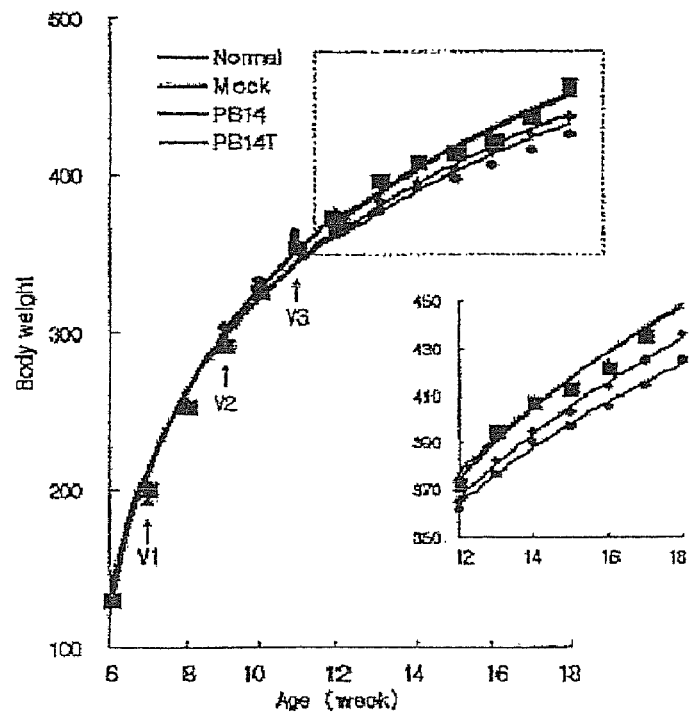
FIG. 15 is a graph showing the body weight increment of SD white rats of normal, mock and vaccinated groups, wherein the normal group (■) was injected with PBS, the mock group (▲) with ovalbumin, a vaccinated group (♦) with ovalbumin-conjugated $PB1_4$ ($PB1_4$+OVA), and another vaccinated group (●) with $PB1_4T$ peptide, each peptide being injected three times at 2-week intervals, the arrows indicating time points at which vaccination was carried out.

Changes in body weight of SD rats after vaccination were plotted on a graph (FIG. 15). From the primary injection to boosting (secondary injection), rats of each group showed similar body weight ranging from 292 g to 297 g. However, from one week after the secondary injection, a difference in body weight of rats was observed between vaccinated groups and normal and mock groups. At 18 weeks of age, compared to the mock groups, the PBl$_4$-vaccinated group showed a difference of 16 g in body weight, and the PBl$_4$T-vaccinated group displayed a difference of 27 g in body weight (Table 2). This indicates that the weak immune responses induced by the primary injection were enhanced after boosting by the secondary injection, that and the enhanced immune responses lead to the suppression of body weight increment of rats. This difference in body weight increment was maintained even after the third injection.

bated at 37° C. for 1 hr. Each well was washed with PEST three times and incubated with a 1:1000 dilution of goat anti-rat IgG as a secondary antibody. The plate was subjected to color development with OPD, and absorbance was measured at 450 nm.

Figure 16:
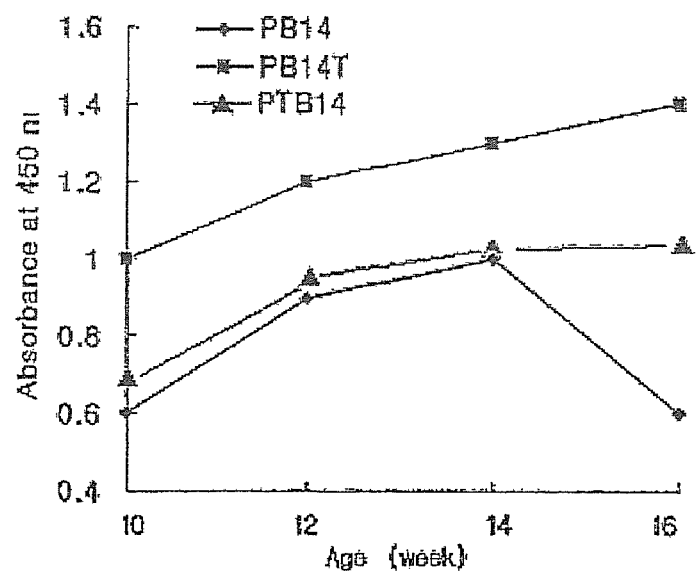
FIG. 16 is a graph showing the changes in titers of anti-PB1 antibodies induced by immunization of $PB1_4$, $PB1_4T$ and $PTB1_4$, respectively.

FIG. 16 shows the antibody titers of SD rats of vaccinated groups at 10, 12, 14 and 16 weeks of age. Titers were determined by ELISA based on the absorbance value of 0.6 when each serum sample was 1:2000 diluted. When the serum sample was diluted at 1:500 to 1:8000, the groups injected with PBl$_4$, PBl$_4$T and PTBl$_4$ showed increased antibody titers until 14 weeks of age. The PBl$_4$T-immunized group displayed 1.5-fold higher O.D. values than the PBl$_4$-immunized group, and the PTBl$_4$-immunized group showed a slight increase compared to the PBl$_4$ group. At 16 weeks of age, the PBl$_4$ group showed a reduction in antibody titer, and the PBl$_4$T and PTBl$_4$ groups maintained the increase of antibody titers. However, PTB1₄ was found to have a remarkably weak effect in increasing antibody titers by about 50-60% compared to PB1₄T.

Example 14

Evaluation of Serum Lipid Profiles

TG and cholesterol levels were measured as follows. 4 μl of a serum sample were mixed with 200 μl of a development reagent and incubated at 37° C. for 5 min, and absorbance was then measured at 505 nm and 500 nm. To measure HDL levels, a serum sample was mixed with a precipitation reagent at a ratio of 1:1, allowed to stand at room temperature for 10 min, and centrifuged at over 3000 rpm for 10 min. 4 μl of the centrifugal supernatant was mixed with 200 μl of a development reagent and incubated at 37° C. for 5 min, and absorbance was then measured at 555 nm. LDL-cholesterol levels were measured using an EZ LDL cholesterol kit (Sigma) and an LDL calibrator (Randox). According to the protocol supplied by the manufacturer, 4 μl of a serum sample was mixed with 1,150 μl of a reagent contained in the kit, incubated at 37° C. for 5 min, supplemented with 250 μl of the reagent, and incubated again at 37° C. for 5 min. Then, absorbance was measured at 600 nm. Serum levels of each lipid were determined using measured absorbance and a standard curve was obtained using standard solutions.

The test results for lipid profiles in serum samples collected five weeks after the third injection into SD rats are given in Table 3, below.

TABLE 3

Serum lipid profiles

|  | TG | HDL-cholesterol | Total cholesterol | LDL-cholesterol |
|---|---|---|---|---|
| Normal | 102.3 ± 5.6 | 51.5 ± 2.7 | 110.2 ± 6.5 | 47.7 ± 9.5 |
| Mock | 98.0 ± 5.9 | 54.6 ± 7.8 | 104.1 ± 3.9 | 42.9 ± 9.1 |
| PB1₄⁺ᴼⱽᴬ | 92.5 ± 4.5 | 41.7 ± 4.3 | 94.6 ± 7.1 | 34.8 ± 4.0 |
| PB1₄T | 90.3 ± 6.2 | 43.0 ± 2.5 | 97.6 ± 2.3 | 33.0 ± 4.3 |

In Table 3, all data are represented as mean±SD, wherein SD (standard deviation) was calculated for five SD white rats, and units are mg/dl.

Figure 17:
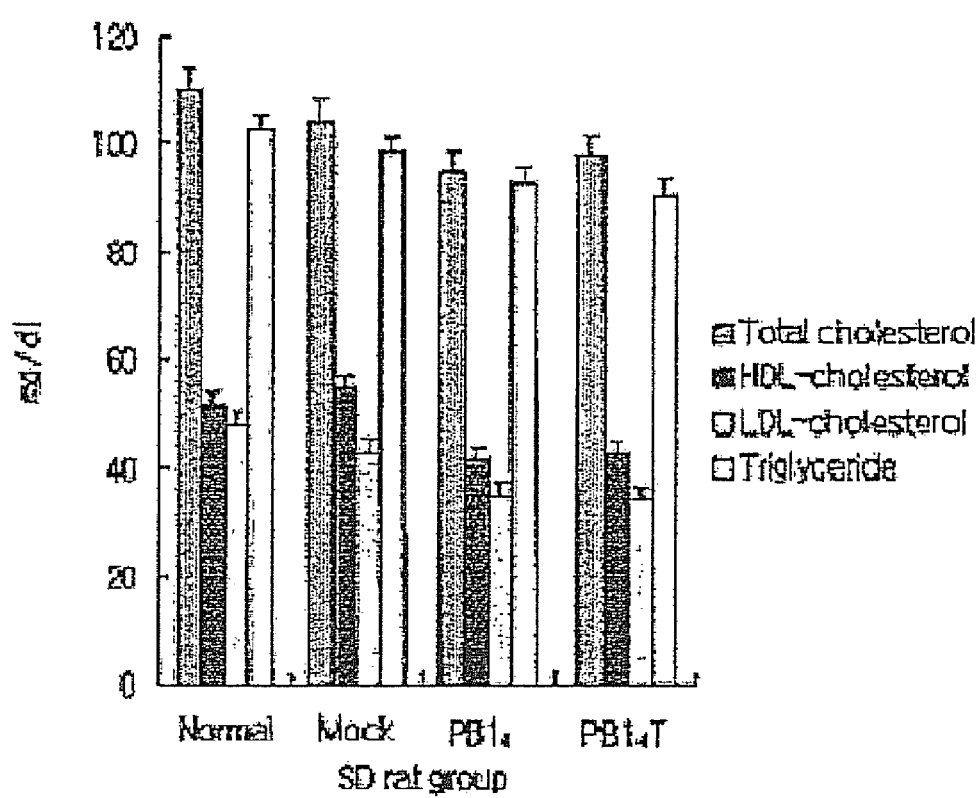
FIG. 17 is a graph showing serum levels of triglyceride, HDL, LDL and total cholesterol.

The normal and mock groups displayed levels of TG and cholesterol about 10 mg/ml (10 mg/100 ml) higher than the vaccinated groups. When the vaccinated groups were compared with each other, higher levels of TG and LDL-cholesterol were found in the PB1₄-vaccinated group but the difference was negligible (FIG. 17).

Example 15

Clinical Test with Pet Dog Subjects

PB1₄T was mixed with alumina as an adjuvant. 0.5 ml of the mixture (2 mg/ml) was intramuscularly or subcutaneously injected into ten pet dogs (managed with an obesity treatment in an animal hospital in Ansan, Korea) twice at 2-week intervals. Changes in body weight of the dogs were observed for a period of 1.5 to 3 months. As a result, an antibody was slowly reduced (half-life: three months), and no increase in body weight was found in the pet dogs even when the dogs were allow to freely eat snacks and high-fat foods. In detail, the body weight increment was suppressed in all of the ten pet dogs even when the dogs digested snacks and high calorie foods. In particular, Yorkshire Terriers did not increase body weight when injected with PB1₄T even in the situation in which the body weight of the dog was predicted to increase according to the dog's sex and age.

In addition, serum samples were collected from the immunized pet dogs to assess the induction degree of antibody responses. One week after the secondary injection, serum titers of an antibody to PB14T and PB1₄ were measured by ELISA. A high absorbance of 0.5 was found even when the serum samples were diluted 5,000-50,000 times, indicating that the PB1₄T peptide has an excellent effect on the induction of antibody responses.

TABLE 4

Changes in body weight after vaccination

| Species | Sex | Age (year) | Body weight (kg) for the test period (wk) | | | | | Diet |
|---|---|---|---|---|---|---|---|---|
| | | | 0 | 2 | 4 | 8 | 12 | |
| Shih Tzu | F | 4.4 | 5.5 | 5.2 | 5.5 | 5.3 | 5.3 | High-calorie |
| Maltese | F | 8 | 4.3 | 4.0 | 4.2 | | | Normal |
| Poodle | F | 7.4 | 4.7 | 4.7 | 4.6 | | | Low-calorie |
| Poodle | F | 6.1 | 4.5 | 4.5 | 4.4 | | | Low-calorie |
| Yorkshire Terrier | F | 4 | 5.9 | 5.6 | 5.6 | | | Normal |
| Yorkshire Terrier | F | 15 | 8.7 | 8.8 | 8.6 | | | High-calorie |
| Yorkshire Terrier | F | 3.7 | 3.8 | 3.8 | 3.7 | | | High-calorie |
| Yorkshire Terrier | M | 5.1 | 4.8 | 4.8 | 4.7 | | | Normal |
| Yorkshire Terrier | M | 2.5 | 3.3 | 3.4 | 3.3 | | | High-calorie |
| Miniature Pinsher | M | 5.1 | 3.6 | 3.5 | 3.5 | | | High-calorie |
| Miniature Schunauzer | F | 1.4 | 7.2 | 7.0 | 7.0 | | | Normal |

INDUSTRIAL APPLICABILITY

As described hereinbefore, the hybrid polypeptide of the present invention, in which a C-terminus of a mimetic peptide of a B cell epitope of apo B-100 having an anti-obesity effect is fused to an N-terminus of a helper T cell epitope, displays an excellent anti-obesity activity without inducing immune responses that neutralize beneficial activities or effects of the B cell epitope of apolipoprotein B-100 or without causing harmful side effects. Therefore, the hybrid polypeptide is very useful in preventing or treating obesity.

The invention claimed is:

1. An immunogenic hybrid polypeptide, in which the C-terminus of a peptide is fused to the N-terminus of a helper T cell epitope, said peptide comprising one or more copies of an amino acid sequence selected from the group consisting of SEQ ID Nos. 1, 2 and 3.

2. The polypeptide according to claim 1, wherein the peptide is prepared by linking two to eight copies of the amino acid sequence selected from the group consisting of SEQ ID Nos. 1, 2 and 3.

3. The polypeptide according to claim 2, wherein the peptide is prepared by linking four copies of the amino acid sequence selected from the group consisting of SEQ ID Nos. 1, 2 and 3.

4. The polypeptide according to claim 3, wherein the peptide is prepared by linking four copies of the amino acid sequence of SEQ ID No. 1.

5. The polypeptide according to claim 4, wherein the peptide is a polypeptide having an amino acid sequence of SEQ ID No. 5.

6. The polypeptide according to claim 1, wherein the helper T cell epitope is selected from the group consisting of hepatitis B surface antigen helper T cell epitopes, *Chlamydia trachomitis* major outer membrane protein helper T cell epitopes, *Plasmodium falciparum* circumsporozoite helper T cell epitopes, *Escherichia coli* TraT helper T cell epitopes, Tetanus toxoid helper T cell epitopes, diphtheria toxoid helper T cell epitopes, *Schistosoma mansoni* triose phosphate isomerase helper T cell epitopes, measles virus F protein helper T cell epitopes, and rabies virus helper T cell epitopes.

7. The polypeptide according to claim 6, wherein the T cell epitope is a helper T cell epitope of the hepatitis B surface antigen.

8. The polypeptide according to claim 7, wherein the T cell epitope is a preS2 helper T cell epitope of the hepatitis B surface antigen.

9. The polypeptide according to claim 8, wherein the T cell epitope has an amino acid sequence of SEQ ID No. 7.

10. The polypeptide according to claim 1, which has an amino acid sequence of SEQ ID No. 9.

11. A immunogenic composition for preventing or treating obesity, comprising the polypeptide of any one of claims 1 to 10.

* * * * *

SEQUENCE LISTING

<160> NUMBER OF SEQ ID NOS: 11

<210> SEQ ID NO 1

```
<211> LENGTH: 15
<212> TYPE: PRT
<213> ORGANISM: Artificial Sequence
<220> FEATURE:
<223> OTHER INFORMATION: Synthesized

<400> SEQUENCE: 1

Arg Asn Val Pro Pro Ile Phe Asn Asp Val Tyr Trp Ile Ala Phe
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthesized

<400> SEQUENCE: 2

Arg Phe Arg Gly Leu Ile Ser Leu Ser Gln Val Tyr Leu Asp Pro
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: Synthesized

<400> SEQUENCE: 3

Ser Val Cys Gly Cys Pro Val Gly His His Asp Val Val Gly Leu
1               5                   10                  15

<210> SEQ ID NO 4
<211> LENGTH: 204
<212> TYPE: DNA
<213> ORGANISM: Artificial Sequence
<220> FEATURE:
<223> OTHER INFORMATION: Synthesized

<400> SEQUENCE: 4
gtcgaccgta atgttcctcc tatcttcaat gatgtttatt ggattgcatt cctcgaccgt    60
aatgttcctc ctatcttcaa tgatgtttat tggattgcat tcctcgaccg taatgttcct   120
cctatcttca atgatgttta ttggattgca ttcctcgacc gtaatgttcc tcctatcttc   180
aatgatgttt attggattgc attc                                          204

<210> SEQ ID NO 5
<211> LENGTH: 68
<212> TYPE: PRT
<213> ORGANISM: Artificial Sequence
<220> FEATURE:
<223> OTHER INFORMATION: Synthesized

<400> SEQUENCE: 5

Val Asp Arg Asn Val Pro Pro Ile Phe Asn Asp Val Tyr Trp Ile Ala
1               5                   10                  15

Phe Leu Asp Arg Asn Val Pro Pro Ile Phe Asn Asp Val Tyr Trp Ile
            20                  25                  30

Ala Phe Leu Asp Arg Asn Val Pro Pro Ile Phe Asn Asp Val Tyr Trp
        35                  40                  45

Ile Ala Phe Leu Asp Arg Asn Val Pro Pro Ile Phe Asn Asp Val Tyr
    50                  55                  60

Trp Ile Ala Phe
65
```

<210> SEQ ID NO 6
<211> LENGTH: 180
<212> TYPE: DNA
<213> ORGANISM: Hepatitis B virus

<400> SEQUENCE: 6

```
atgcagtgga actccaccac attccaccaa gctctgctag atcccagagt gagggcccta      60
tattttcctg ctggtggctc cagttccgga acagtaaacc ctgttccgac tactgcctca     120
cccatatcgt caatcttctc gaggactggg daccctgcac cgaacctcga gcggtcataa     180
```

<210> SEQ ID NO 7
<211> LENGTH: 59
<212> TYPE: PRT
<213> ORGANISM: Hepatitis B virus

<400> SEQUENCE: 7

Met Gln Trp Asn Ser Thr Thr Phe His Gln Ala Leu Leu Asp Pro Arg
1               5                   10                  15

Val Arg Gly Leu Tyr Phe Pro Ala Gly Gly Ser Ser Gly Thr Val
            20                  25                  30

Asn Pro Val Pro Thr Thr Ala Ser Pro Ile Ser Ser Ile Phe Ser Arg
        35                  40                  45

Thr Gly Asp Pro Ala Pro Asn Leu Glu Arg Ser
    50                  55

<210> SEQ ID NO 8
<211> LENGTH: 438
<212> TYPE: DNA
<213> ORGANISM: Artificial Sequence
<220> FEATURE:
<223> OTHER INFORMATION: Synthesized

<400> SEQUENCE: 8

```
atgagaggat cgcatcacca tcacggatcc gatgatgatg acaagatcgt cgaccgtaat      60
gttcctccta tcttcaatga tgtttattgg attgcattcc tcgaccgtaa tgttcctcct     120
atcttcaatg atgtttattg gattgcattc ctcgaccgta atgttcctcc tatcttcaat     180
gatgtttatt ggattgcatt cctcgaccgt aatgttcctc ctatcttcaa tgatgtttat     240
tggattgcat tcctcgacat gcagtggaac tccaccacat tccaccaagc tctgctagat     300
cccagagtga gggcctata ttttcctgct ggtggctcca gttccggaac agtaaaccct     360
gttccgacta ctgcctcacc catatcgtca atcttctcga ggactgggga ccctgcaccg     420
aacctcgagc ggtcataa                                                    438
```

<210> SEQ ID NO 9
<211> LENGTH: 147
<212> TYPE: PRT
<213> ORGANISM: Artificial Sequence
<220> FEATURE:
<223> OTHER INFORMATION: Synthesized

<400> SEQUENCE: 9

Met Arg Gly Ser His His His His His His Gly Ser Asp Asp Asp Asp
1               5                   10                  15

Leu Ile Val Asp Arg Asn Val Pro Pro Ile Phe Asn Asp Val Tyr Trp
            20                  25                  30

Ile Ala Phe Leu Asp Arg Asn Val Pro Pro Ile Phe Asn Asp Val Tyr
        35                  40                  45

Trp Ile Ala Phe Leu Asp Arg Asn Val Pro Pro Ile Phe Asn Asp Val

```
                50                  55                  60
Tyr Trp Ile Ala Phe Leu Asp Arg Asn Val Pro Pro Ile Phe Asn Asp
 65                  70                  75                  80

Val Tyr Trp Ile Ala Phe Leu Asp Met Gln Trp Asn Ser Thr Thr Phe
                    85                  90                  95

His Gln Ala Leu Leu Asp Pro Arg Val Arg Gly Leu Tyr Phe Pro Ala
                100                 105                 110

Gly Gly Ser Ser Ser Gly Thr Val Asn Pro Val Pro Thr Thr Ala Ser
                115                 120                 125

Pro Ile Ser Ser Ile Phe Ser Arg Thr Gly Asp Pro Ala Pro Asn Leu
            130                 135                 140

Glu Arg Ser
145

<210> SEQ ID NO 10
<211> LENGTH: 432
<212> TYPE: DNA
<213> ORGANISM: Artificial Sequence
<220> FEATURE:
<223> OTHER INFORMATION: Synthesized

<400> SEQUENCE: 10
atgagaggat cgcatcacca tcaccatcac ggatccgatg atgatgacaa gatcgtcgac      60
atgcagtgga actccaccac attccaccaa gctctgctag atcccagagt gaggggccta     120
tattttcctg ctggtggctc cagttccgga acagtaaacc ctgttccgac tactgcctca     180
cccatatcgt caatcttctc gaagactggg gaccctgcac cgaacctcga ccgtaatgtt     240
cctcctatct tcaatgatgt ttattggatt gcattcctcg accgtaatgt tcctcctatc     300
ttcaatgatg tttattggat tgcattcctc gaccgtaatg ttcctcctat cttcaatgat     360
gtttattgga ttgcattcct cgaccgtaat gttcctccta tcttcaatga tgtttattgg     420
attgcattct aa                                                         432

<210> SEQ ID NO 11
<211> LENGTH: 143
<212> TYPE: PRT
<213> ORGANISM: Artificial Sequence
<220> FEATURE:
<223> OTHER INFORMATION: Synthesized

<400> SEQUENCE: 11

Met Arg Gly Ser His His His His His His Gly Ser Asp Asp Asp
  1               5                  10                  15

Leu Ile Val Asp Met Gln Trp Asn Ser Thr Thr Phe His Gln Ala Leu
                    20                  25                  30

Leu Asp Pro Arg Val Arg Gly Leu Tyr Phe Pro Ala Gly Gly Ser Ser
                35                  40                  45

Ser Gly Thr Val Asn Pro Val Pro Thr Thr Ala Ser Pro Ile Ser Ser
 50                  55                  60

Ile Phe Ser Leu Thr Gly Asp Pro Ala Pro Asn Leu Asp Arg Asn Val
 65                  70                  75                  80

Pro Pro Ile Phe Asn Asp Val Tyr Trp Ile Ala Phe Leu Asp Arg Asn
                    85                  90                  95

Val Pro Pro Ile Phe Asn Asp Val Tyr Trp Ile Ala Phe Leu Asp Arg
                100                 105                 110
```

```
Asn Val Pro Pro Ile Phe Asn Asp Val Tyr Trp Ile Ala Phe Leu Asp
        115                 120                 125

Arg Asn Val Pro Pro Ile Phe Asn Asp Val Tyr Trp Ile Ala Phe
    130                 135                 140
```